(12) United States Patent
Hsiao et al.

(10) Patent No.: US 11,970,688 B2
(45) Date of Patent: Apr. 30, 2024

(54) INTEGRATED CELL MONITORING APPARATUS AND METHOD OF USING THE SAME

(71) Applicant: Taiwan Semiconductor Manufacturing Co., Ltd., Hsinchu (TW)

(72) Inventors: Yi-Hsing Hsiao, Hsinchu (TW); Jui-Cheng Huang, Hsinchu (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 593 days.

(21) Appl. No.: 16/944,140

(22) Filed: Jul. 30, 2020

(65) Prior Publication Data

US 2022/0033759 A1 Feb. 3, 2022

(51) Int. Cl.
*C12M 1/34* (2006.01)
*C12M 1/00* (2006.01)
(Continued)

(52) U.S. Cl.
CPC ............ *C12M 41/38* (2013.01); *C12M 21/08* (2013.01); *C12M 23/16* (2013.01); *C12M 23/38* (2013.01);
(Continued)

(58) Field of Classification Search
None
See application file for complete search history.

(56) References Cited

U.S. PATENT DOCUMENTS

| 8,728,844 B1 * | 5/2014 | Liu | ............... H01L 29/66477 257/253 |
| 2020/0055054 A1 * | 2/2020 | Hajipouran Benam | .. B01L 9/50 |

FOREIGN PATENT DOCUMENTS

| CN | 102337213 | 2/2012 |
| CN | 103333802 | 10/2013 |

(Continued)

OTHER PUBLICATIONS

Moshksayan et al. "Spheroids-on-a-chip: Recent advances and design considerations inmicrofluidic platforms for spheroid formation and cultureKhashayar", Sensors and Actuators B 263 (2018) 151-176. (Year: 2018).*

(Continued)

*Primary Examiner* — William H. Beisner
(74) *Attorney, Agent, or Firm* — JCIPRNET

(57) ABSTRACT

Cell monitoring apparatus includes sensing chip and channel module. Sensing chip includes channel region, source and drain regions, and sensing film. The channel region includes first semiconductor material. The source and drain regions are disposed at opposite sides of the channel region, and include a second semiconductor material. Sensing film is disposed on the channel region at a sensing surface of the sensing chip. Channel module is disposed on the sensing surface of sensing chip. A microfluidic channel is formed between the sensing surface of the sensing chip and a proximal surface of the channel module. The microfluidic channel includes a culture chamber and a micro-well. The culture chamber is concave into the proximal surface of the channel module, and overlies the channel region. The micro-well is concave into a side of the culture chamber, and directly faces the sensing film.

20 Claims, 20 Drawing Sheets

(51) Int. Cl.
*C12M 3/00* (2006.01)
*C12M 3/06* (2006.01)
*C12N 5/00* (2006.01)
*G01N 33/50* (2006.01)

(52) U.S. Cl.
CPC ....... *C12N 5/0062* (2013.01); *G01N 33/5005* (2013.01); *C12N 2513/00* (2013.01)

(56) References Cited

FOREIGN PATENT DOCUMENTS

| CN | 108485972 | | 9/2018 |
|---|---|---|---|
| CN | 110954585 | | 4/2020 |
| JP | 2017148001 A | * | 8/2017 |
| WO | 2019145847 | | 8/2019 |

OTHER PUBLICATIONS

Ziolkowska et al. "Long-term three-dimensional cel Iculture and anticancer drug activity evaluation in a microfluidic chip." Biosensors and Bioelectronics 40 (2013) 68-74. (Year: 2013).*

Fang Yu, et al., "A perfusion incubator liver chip for 3D cell culture with application on chronic hepatotoxicity testing." Scientific Reports, vol. 7, Nov. 6, 2017, pp. 1-16.

Andrea Pavesi, et al., "Controlled electromechanical cell stimulation on a trip." Scientific Reports, vol. 5, Jul. 2, 2015, pp. 1-12.

Brian R. Dorvel, et al., "Silicon Nanowires with High-k Hafnium Oxide Dielectrics for Sensitive Detection of Small Nucleic Acid Oligomers." 2012 American Chemical Society Nano, Jun. 2012, pp. 1-28.

Donglai LV, et al., "Three-dimensional cell culture A powerful tool in tumor research and drug discovery (Review)" Oncology Letters, vol. 14, Jul. 2017, pp. 6999-7010.

"Office Action of China Counterpart Application", dated Nov. 18, 2023, p. 1-p. 12.

* cited by examiner

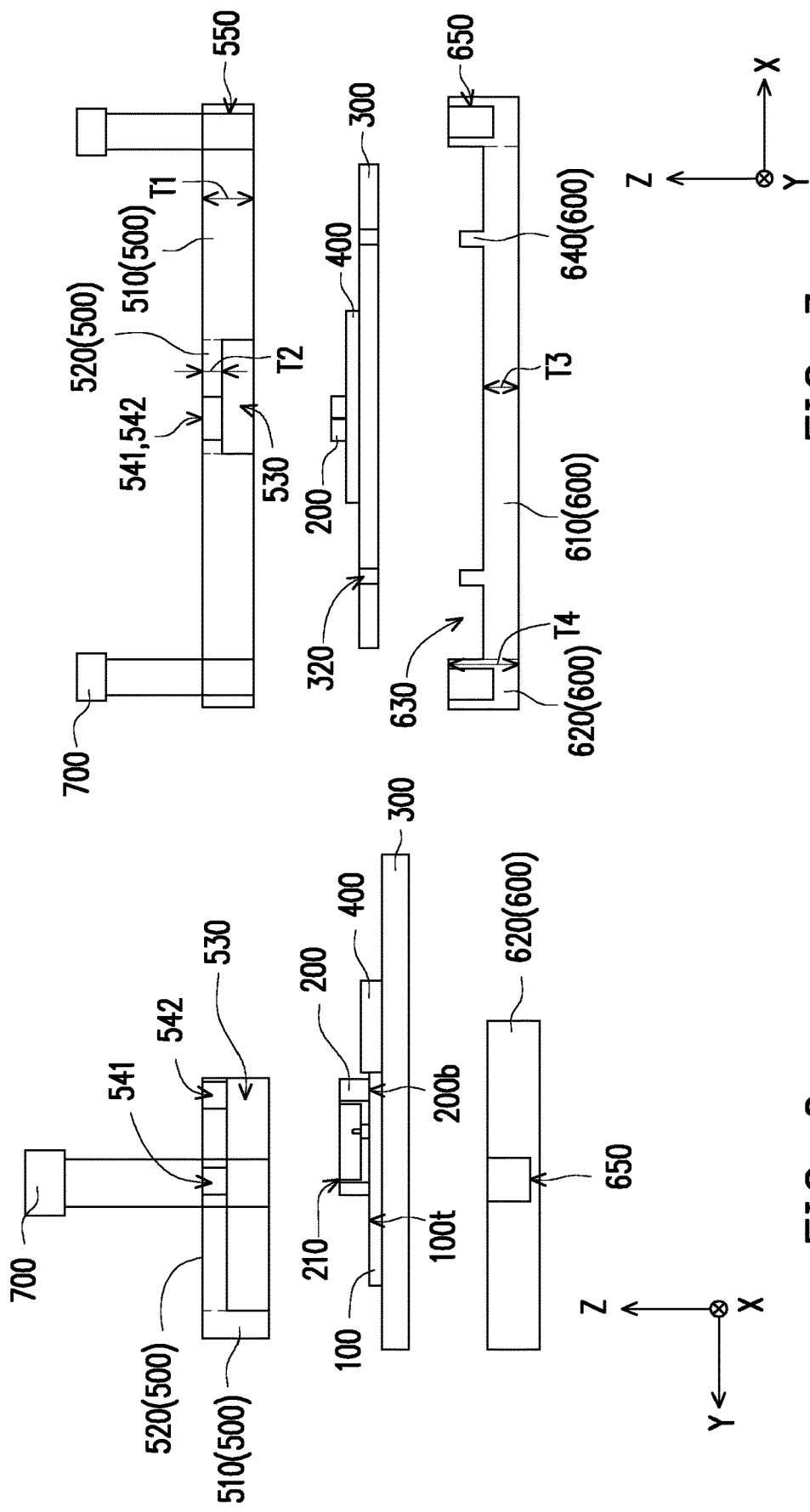

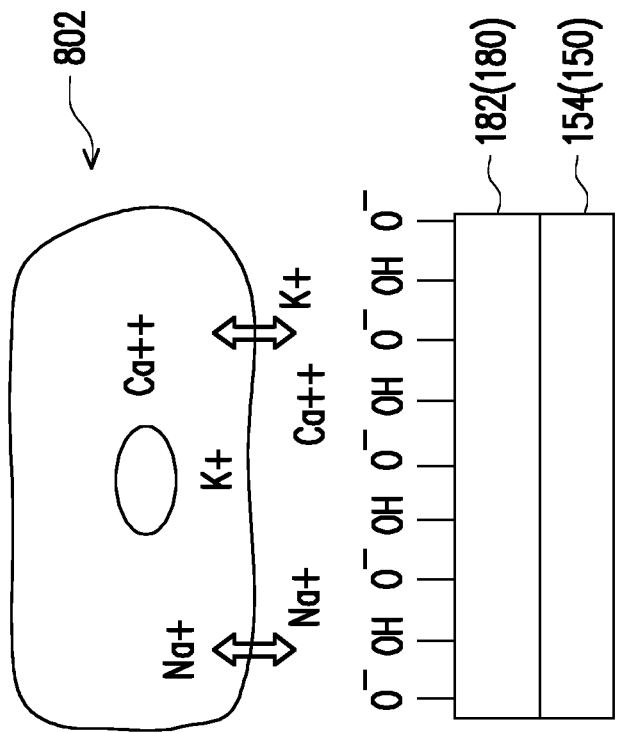
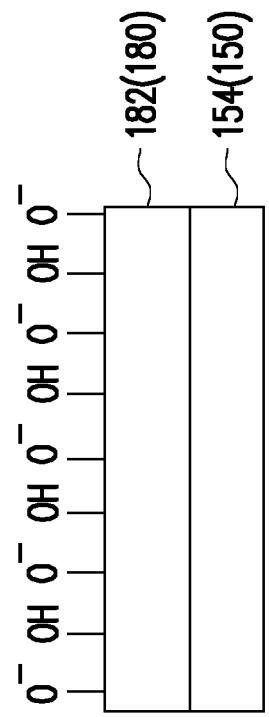
FIG. 9B
FIG. 9A

INTEGRATED CELL MONITORING APPARATUS AND METHOD OF USING THE SAME

BACKGROUND

Three-dimensional cellular aggregates have received considerable attention in view of their potential application, for example in the pharmaceutical industry, for the possibility they offer to perform tests on samples phylogenetically closer to the target organisms (e.g., humans) than animal models (e.g., rodents). Techniques employing three-dimensional cellular aggregates are actively researched to increase the accuracy and clinical relevance of the performed experiments.

BRIEF DESCRIPTION OF THE DRAWINGS

Aspects of the disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 2 is a schematic exploded side view of a cell monitoring apparatus according to some embodiments of the disclosure.

FIG. 3 is a schematic exploded side view of a cell monitoring apparatus according to some embodiments of the disclosure.

FIG. 9A, FIG. 10A, and FIG. 11A are schematic perspective views of sensing films according to some embodiments of the disclosure.

FIG. 9B, FIG. 10B, and FIG. 11B are schematic illustrations of the sensing films of FIG. 9A, FIG. 10A, FIG. 11A, respectively, interacting with a target analyte.

DETAILED DESCRIPTION

Figure 1:
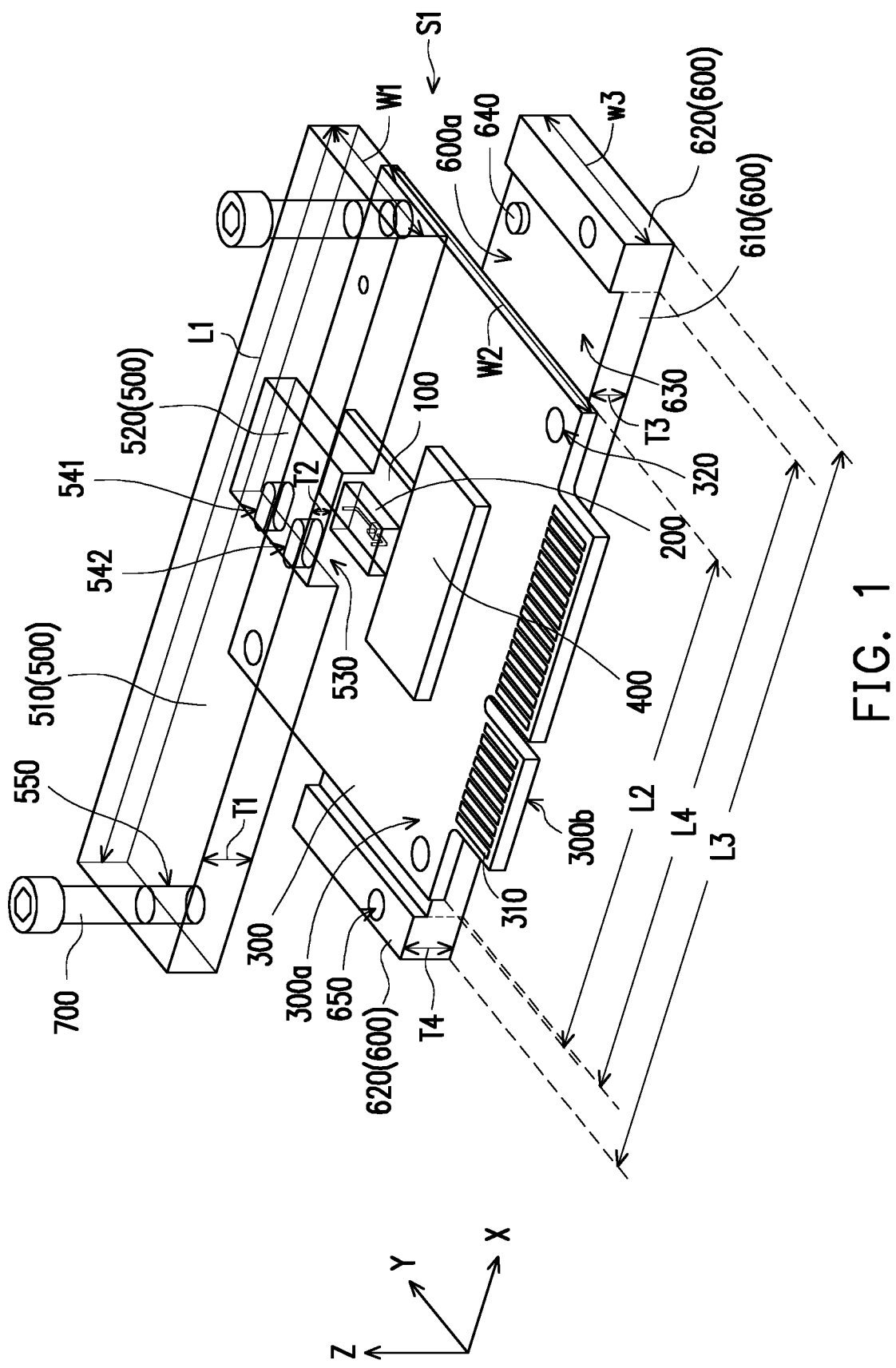
FIG. 1 is a schematic perspective exploded view of a cell monitoring apparatus according to some embodiments of the disclosure.

The following disclosure provides many different embodiments, or examples, for implementing different features of the provided subject matter. Specific examples of components and arrangements are described below to simplify the disclosure. These are, of course, merely examples and are not intended to be limiting. For example, the formation of a second feature over or over a first feature in the description that follows may include embodiments in which the second and first features are formed in direct contact, and may also include embodiments in which additional features may be formed between the second and first features, such that the second and first features may not be in direct contact. In addition, the disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath", "below", "lower", "on", "over", "overlying", "above", "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Figure 4:
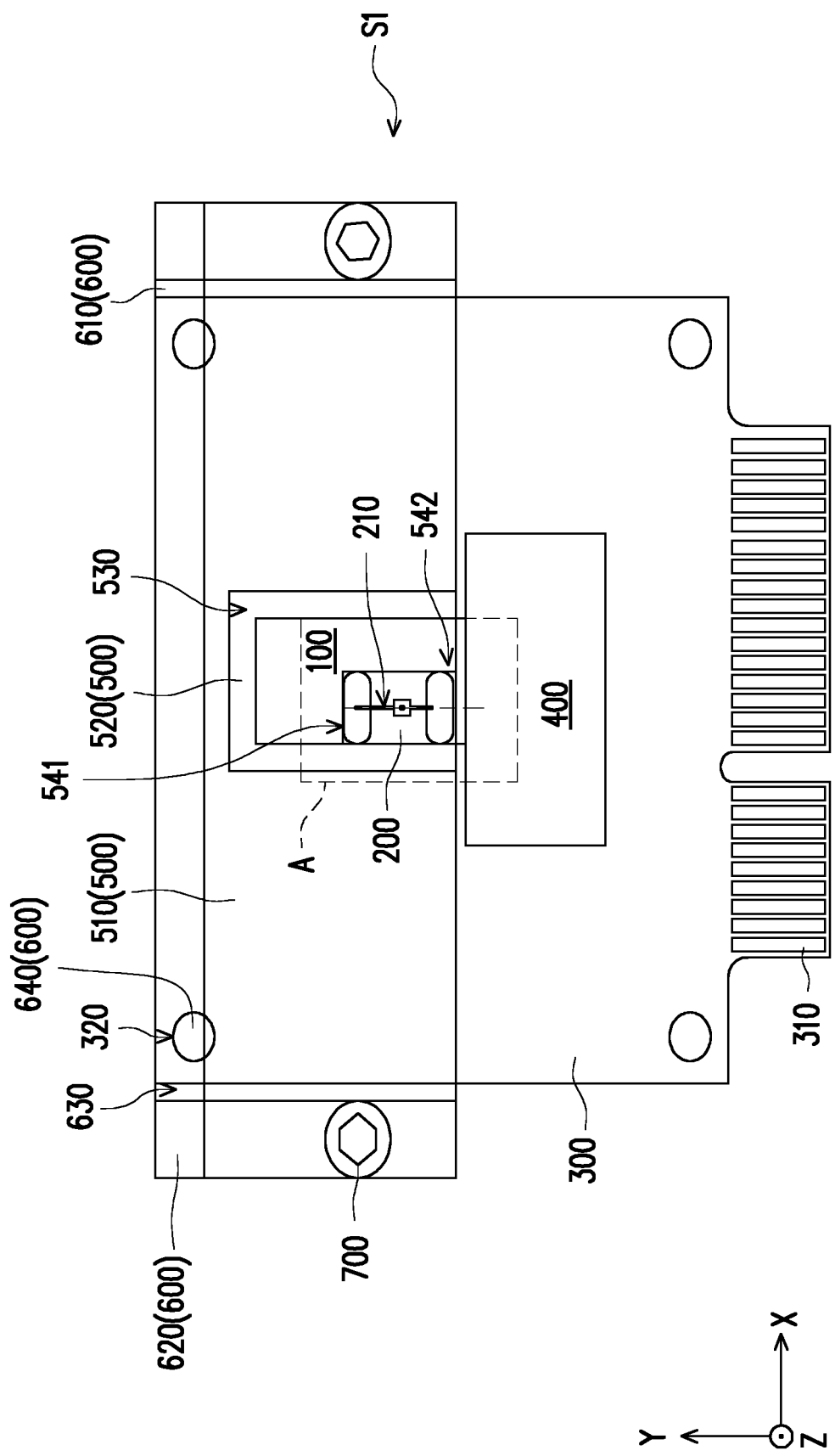
FIG. 4 is a schematic top-view of a cell monitoring apparatus according to some embodiments of the disclosure.

In FIG. 1 is illustrated a schematic perspective exploded view of a cell monitoring apparatus S1 according to some embodiments of the disclosure. In FIG. 1 are also illustrated the axes of the orthogonal directions X, Y, and Z of a local coordinate system of the cell monitoring apparatus S1 according to some embodiments of the disclosure. FIG. 2 is a schematic exploded side view of the cell monitoring apparatus S1 viewed along the X direction according to some embodiments of the disclosure. FIG. 3 is a schematic exploded side view of the cell monitoring apparatus S1 viewed along the Y direction according to some embodiments of the disclosure. FIG. 4 is a schematic top view of the cell monitoring apparatus S1 according to some embodiments of the disclosure. Referring to FIG. 1 to FIG. 4, the cell monitoring apparatus S1 includes a sensing chip 100 and a channel module 200 disposed on the sensing chip 100. The channel module 200 is disposed on at least a portion of the sensing chip 100. In some embodiments, the footprint of the channel module 200 is smaller than the footprint of the sensing chip 100, and, when assembled, the footprint of the channel module 200 may entirely fall over the sensing chip 100. When the channel module 200 is disposed on the sensing chip 100, a microfluidic channel 210 may be formed between the bottom surface 200b of the channel module 200 and the top surface 100t of the sensing chip 100. In some embodiments, the bottom surface 200b of the channel module 200 may be referred to as a surface of the channel module 200 proximal to the sensing chip 100. In some embodiments, the top surface 100t of the sensing chip 100 may be referred to as a sensing surface of the sensing chip 100. In some embodiments, the channel module 200 may be made of a polymeric material. For example, the channel module 200 may be made of polydimethylsiloxane (PDMS).

In some embodiments, the sensing chip 100 may be disposed on a carrier substrate 300. In some embodiments, the carrier substrate 300 may be a circuit carrier, such as a printed circuit board or the like, and the sensing chip 100 may be electrically connected to the carrier substrate 300. For example, the sensing chip 100 may be flip-chip bonded on a surface 300a of the carrier substrate 300. The carrier substrate 300 may include connecting pins 310, which may be used to interface the carrier substrate 300 (and the sensing chip 100) to other electronic devices.

In some embodiments, one or more additional chips (e.g., the chip 400) may be bonded on the surface 300a of the carrier substrate 300 beside the sensing chip 100. In some embodiments, the chip 400 is connected to the sensing chip 100 via the carrier substrate 300. In some embodiments, the chip 400 may be a micro control unit (MCU) die, an input-output (I/O) die, a baseband (BB) die, or the like. For example, the chip 400 may pre-process the signal received from the sensing chip 100 before it is transmitted to other electronic devices (e.g., a control station, a data analysis station, or the like) through the connecting pins 310. In some embodiments, the functions of the chip 400 may be performed in some regions of the sensing chip 100. In some embodiments, the additional chips 400 are optional, and may be omitted.

In some embodiments, a cover module 500 may be disposed on the carrier substrate 300, on the surface 300a. The cover module 500 may have an elongated footprint (e.g., a rectangular footprint), and may extend on the carrier substrate 300, over the sensing chip 100 and the channel module 200. In some embodiments, a ratio of the length L1 along the X direction to the width W1 along the Y direction of the cover module 500 may be in the range from 3 to 5. For example, the length L1 may be in the range from 1.5 cm to 6.0 cm, and the width W1 may be in the range from 0.5 cm to 2.0 cm. In some embodiments, the length L1 of the cover module 500 may be larger than the length L2 of the carrier substrate 300 along the X direction, while the width W2 of the carrier substrate 300 along the Y direction may be greater than the width W1 of the cover module 500. That is, the cover module 500 may cover a portion of the carrier substrate 300, while the remaining portion of the carrier substrate 300 may be left exposed. For example, the cover module 500 may extend over the area of the carrier substrate 300 in which the channel module 200 and the sensing chip 100 are located, while the additional chip(s) 400 and the connecting pins 310 may be left exposed by the cover module 500.

In some embodiments, the cover module 500 includes a region 510 of thickness T1 and a region 520 of thickness T2. The thickness T1 and the thickness T2 are both measured along the Z direction, and the thickness T1 is greater than the thickness T2. The region 510 of thickness T1 is adjacent to the region 520 of thickness T2. In some embodiments, the region 520 of thickness T2 extends over the sensing chip 100 and the channel module 200. The region 510 of thickness T1 extends on opposite sides of the region 520 along the X direction. In some embodiments, the region 510 extends along three sides of the region 520, namely at opposite sides with respect to the X direction and on one side with respect to the Y direction. That is, in some embodiments the region 520 results in the cover module 500 including a recess 530 in which the sensing chip 100 and the channel module 200 are accommodated. The region 520 of reduced thickness T2 may extend at least as much as the footprint of the sensing chip 100. In some embodiments, a ratio between the length L1 and the thickness T1 may be in the range from 12 to 15.

In some embodiments, a ratio between the width W1 and the thickness T1 may be in the range from 0.4 to 5. In some embodiments, the thickness T1 may be in the range from 0.1 to 0.5 cm.

The cover module 500 may contact the carrier substrate 300 in correspondence of the region 510. The ends along the X direction of the region 510 may protrude with respect to the underlying carrier substrate 300. In some embodiments, the carrier module 500 includes through holes 541, 542 in the region 520, in correspondence of the channel module 200. In some embodiments, the cover module 500 includes a polymeric material. For example, a material of the cover module 500 may include polymethylmethacrylate (PMMA).

In some embodiments, a base module 600 may be disposed on an opposite side 300b of the circuit substrate 300 with respect to the cover module 500. The base module 600 may have similar dimensions to the cover module 500. That is, at least a portion of the circuit substrate 300 may be sandwiched between the base module 600 and the cover module 500. For example, the length L3 of the base module along the X direction may be 3 to 5 times larger than the width W3 of the base module 600 along the Y direction, and the length L3 may be larger than the length L2 of the carrier substrate 300. Furthermore, the width W2 of the carrier substrate 300 may be larger than the width W3. As such, the carrier substrate 300 may protrude on one or both sides along the Y direction with respect to both the cover module 500 and the base module 600. In some embodiments, the base module 600 includes a region 610 of thickness T3 and a region 620 of thickness T4. The thickness T3 and the thickness T4 are measured along the Z direction, and the thickness T3 is smaller than the thickness T4. In some embodiments, the ratio of the length L3 to the thickness T4 may be in the range from 12 to 15, and the ratio of the width W3 to the thickness T4 may be in the range from 4 to 5. In some embodiments, the thickness T4 may be in the range from 0.1 cm to 0.5 cm.

In some embodiments, the region 620 extends at opposite sides of the region 610 along the X direction, defining a recess 630 in the base module 600 in which the carrier substrate 300 is accommodated. In some embodiments, the recess 630 may extend along the Y direction for the entire width W3 of the base module 600. In the X direction, the region 610 has a length L4 which may be equal to or greater than the length L2 of the carrier substrate 300. That is, the region 610 may extend along the X direction at least as much as the carrier substrate 300, with the region 620 extending further along the X direction with respect to the carrier substrate 300. That is, the region 620 may protrude from both sides along the Y direction from below the carrier substrate 300. In some embodiments, a material of the base module 600 may include a polymeric material. For example, the material of the base module 600 may include polymethylmethacrylate (PMMA). In some embodiments, the base module 600 and the cover module 500 may be made of the same material. In some embodiments, the material of the channel module 200 may be different from the material of one or both of the base module 600 and the cover module 500.

In some embodiments, one or more engaging mechanisms may be included to mechanically couple the carrier substrate 300 with one or both of the cover module 500 and the base module 600, as well as the cover module 500 with the base module 600. For example, the base module 600 may include one or more engaging members 640 protruding along the Z direction in the region 610. The engaging members 640 may be received in holes 320 formed in the carrier substrate 300, so as to fix the carrier substrate 300 with respect to the base member 600. The holes 320 may be through holes, or may be recesses in which the engaging members 640 are accommodated. However, the disclosure is not limited thereto. For example, in some alternative embodiments, the engaging members may be formed on the carrier substrate 300, and the receiving holes or recesses may be formed on the base module 600. Similar engaging mechanisms (not shown) may be provided between the carrier substrate 300 and the cover module 500. In some embodiments, mechanical coupling between the cover module 500 and the base module 600 may involve forming through holes in one or both of the cover module 500 and the base module 600 and fixing the two modules together via fasteners 700 (e.g., screws or bolts) inserted in the through holes. For example, fastening holes 550 may be formed in the region 510 of the cover module 500 outside the footprint of the carrier substrate 300, at a point in which the cover module 500 directly overlies the base module 600. Receiving holes 650 may be formed in the region 620 of the base module 600 in correspondence of the fastening holes 550. Depending on the type of fastener 700 used, the receiving holes 650 may be threaded or smooth, and may be through holes or blind holes. For examples, screws or bolts used as fasteners 700 may pass through the fastening holes 550 and be received in blind threaded receiving holes 650. Alternatively, the receiving holes 650 may also be through holes, and the screws or bolts used as fasteners 700 may be kept in place with nuts (not shown). In some yet alternative embodiments, the receiving holes 650 may be through holes aligned with blind fastening holes 550 formed in the cover module 500. However, the disclosure is not limited by the type, number, or position of engaging mechanisms between the carrier substrate 300, the cover module 500 and the base module 600 as long as the engaging mechanisms do not obstruct or interfere with the microfluidic channel 210 described below. For example, the cover module 500 and the base module 600 may engage with each other through hooks and pins provided along some of the outer surfaces, or through any other suitable mechanism.

Figure 5:
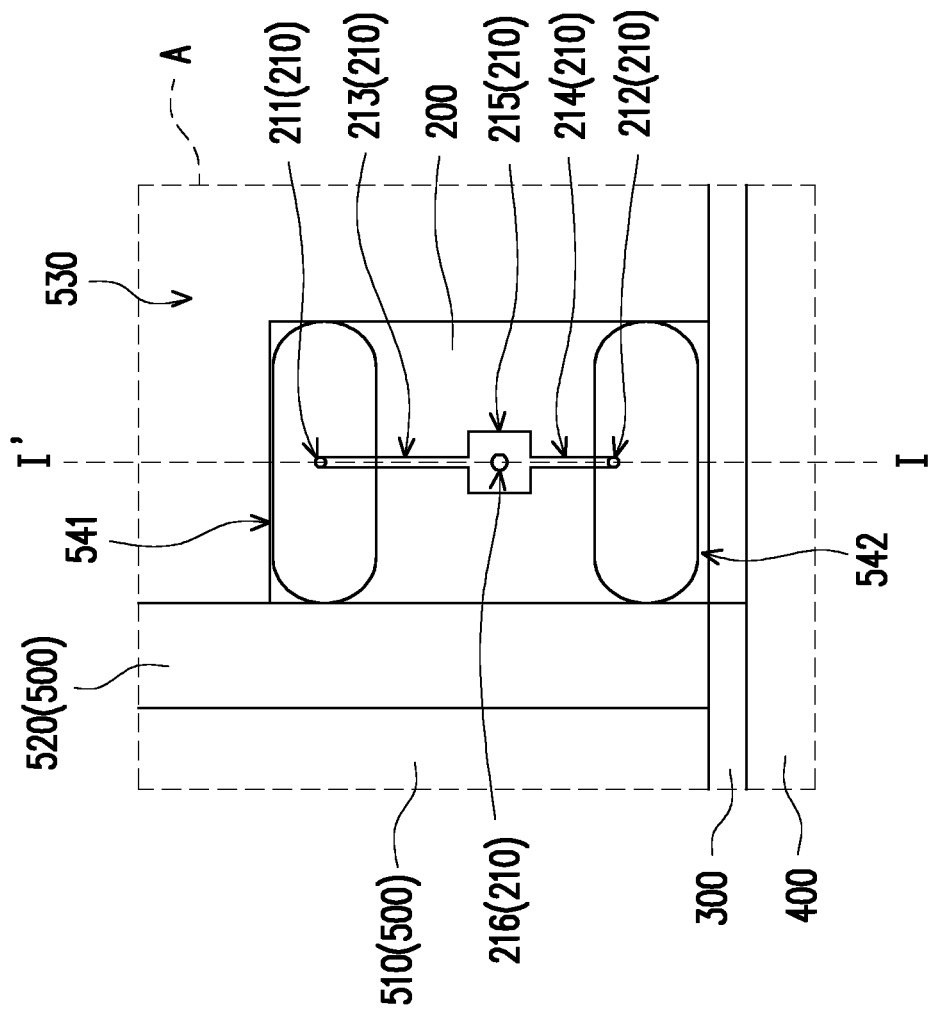
FIG. 5 is an enlarged view of a portion of the schematic top-view of the cell monitoring apparatus of FIG. 4 according to some embodiments of the disclosure.
Figure 6:
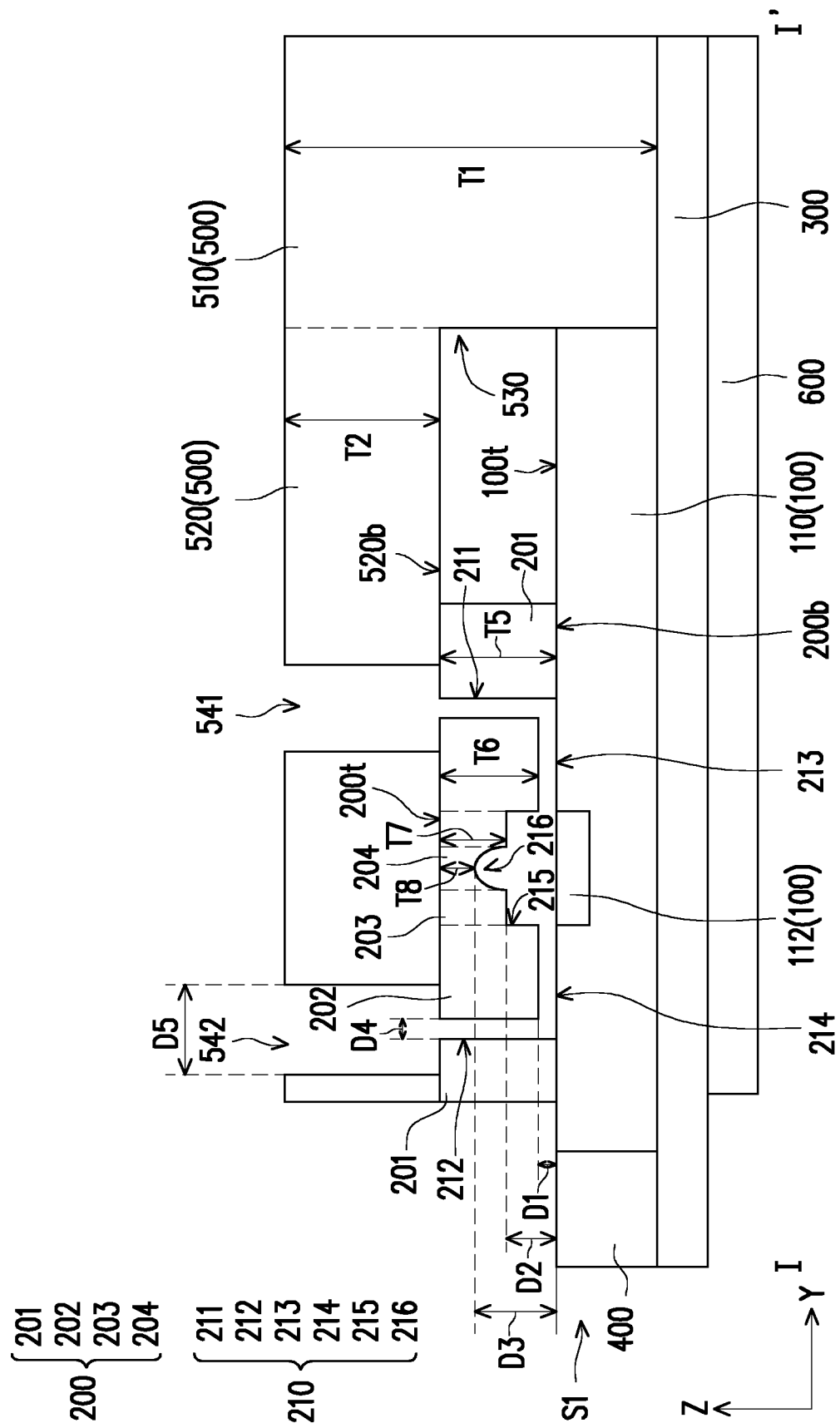
FIG. 6 is a schematic cross-sectional view of a portion of a cell monitoring apparatus according to some embodiments of the disclosure.
Figure 7:
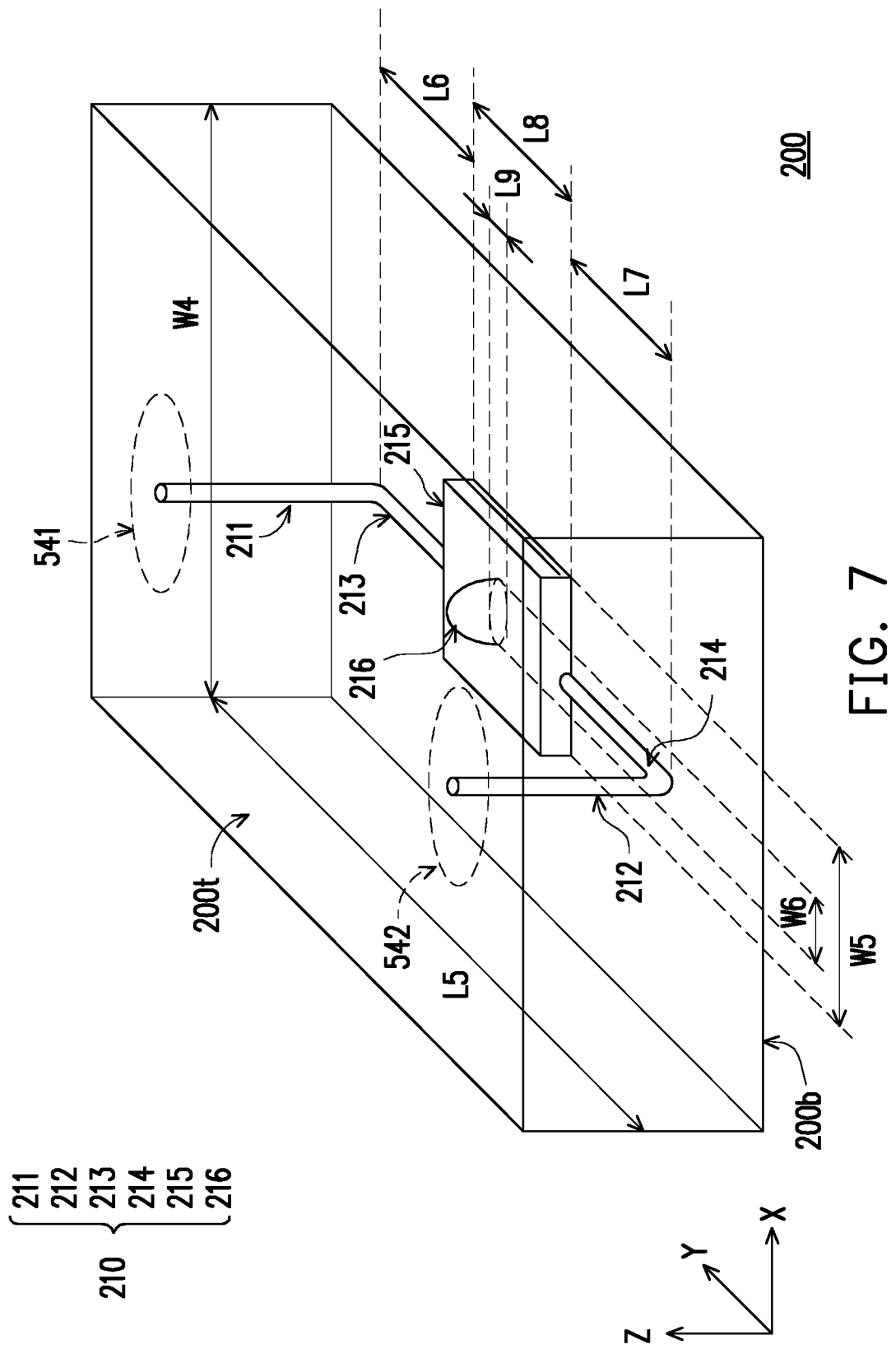
FIG. 7 is a schematic perspective view of a channel module according to some embodiments of the disclosure.

FIG. 5 is an enlarged view of the area A illustrated in the top view of FIG. 4. FIG. 6 is a schematic cross-sectional view of the of the area A illustrated in FIG. 5, taken along a YZ plane at the level height of the line I-I' along the X direction illustrated in FIG. 5. FIG. 7 is a perspective three-dimensional view of the channel module 200 according to some embodiments of the disclosure. Referring to FIG. 5 to FIG. 7, in some embodiments the bottom surface 200b of the channel module 200 and the top surface 100t of the sensing chip 100 define a microfluidic channel 210. In some embodiments, the bottom surface 200b has a structured profile, so as to determine the shape of the microfluidic channel 210. In some embodiments, the channel module 200 includes a pair of microchannels 211, 212 extending across the channel module 200 in the thickness direction (the Z direction illustrated in FIG. 7, normal to the top surface 100t of the sensing chip 100). In some embodiments, the microchannels 211, 212 extend from the top surface 200t of the channel module 200 to the opposite bottom surface 200b. That is, the microchannels 211, 212 extend through the entire thickness T5 of the channel module 200. In some embodiments, the microchannels 211, 212 are offset with respect to each other along at least one of the Y direction or the X direction. For example, as illustrated in FIG. 7, the channel module 200 may have an elongated shape, resembling a parallelepiped, with a longer dimension extending along the Y direction and a shorter dimension extending along the X direction. For example, a ratio of the length L5 of the channel module 200 along the Y direction to the width W4 of the channel module 200 along the X direction may be in the range from 1 to 3. In some embodiments, the length L5 and the width W4 may independently be in the range from 0.05 cm to 0.5 cm.

In some embodiments, the microchannels 211, 212 may be disposed at different level heights (be offset) along the Y direction, while being disposed at the same level height (be aligned) along the X direction. In some alternative embodiments, the microchannels 211, 212 may be offset along both the X direction and the Y direction. In some embodiments, the microchannels 211, 212 may constitute the two ends of the microfluidic channel 210. The bottom surface 200b of the channel module 200 may include one or more recesses defining a structured profile raised with respect to the top surface 100t of the sensing chip 100, so that when the channel module 200 is disposed on the sensing chip 100, the microchannels 211, 212 are in fluidic communication with each other. For example, the channel module 200 may include a region 201 of thickness T5 surrounding the microfluidic channel 210. The region 201 may contact the sensing chip 100 on one side along the Z direction, and the cover module 500 on the opposite side along the Z direction. Regions 202 of thickness T6 smaller than the thickness T5 may be formed between the microchannels 211. The regions 202 of thickness T6 may be in contact with the cover module 500 on one side along the Z direction, while at the opposite side along the Z direction may be separated by a distance D1 from the top surface 100t of the sensing chip 100. That is, the bottom surface 200b may have a recessed profile in correspondence of the region 202, so that it is separated by a distance D1 along the Z direction from the top surface 100t of the sensing chip 100. The distance D1 may be considered as the depth (or diameter) of microchannels 213, 214 formed between the bottom surface 200b of the channel module 200 and the top surface 100t of the sensing chip 100. In some embodiments, the distance D1 corresponds to the difference between the thickness T5 and the thickness T6 of the regions 201 and 202 of the channel module 200.

In some embodiments, the elongated recess (microtrench) forming the microchannel 213 may extend at the bottom surface 200b of the channel module 200 along the Y direction, from the end of the microchannel 211 towards the microchannel 212 for a length L6. Similarly, the elongated recess (microtrench) forming the microchannel 214 may extend at the bottom surface 200b of the channel module 200 along the Y direction, from the end of the microchannel 212 towards the microchannel 211, for a length L7. For example, the microchannel 213 may be formed by an hemicylindrical recess formed at the bottom surface 200b of the channel module 200. One end of the hemicylindrical recesses forming the microchannel 213 may coincide with the end of the microfluidic channel 211, so that the microchannel 213 and the microchannel 211 are attached to each other. The other end of the hemicylindrical recess forming the microchannel 213 may open in a recess of depth D2 forming a culture chamber 215 in correspondence of a region 203 of the channel module 200. Similarly, the microchannel 214 may be formed by another hemicylindrical recess extending from the end of the microchannel 212 to the culture chamber 215. Therefore, the microchannel 213 establishes fluidic communication between the microchannel 211 and the culture chamber 215, while the microchannel 214 establishes fluidic communication between the microchannel 212 and the culture chamber 215. It should be noted that while in the drawings the microchannels 213, 214 are shown as extending substantially straight along the Y direction, the disclosure is not limited thereto. For example, the microtrenches forming the microchannels 213, 214 may be bent, so that a section of a microchannel extends along the Y direction, and another section of the same microchannel may extend along the X direction. In some embodiments, the culture chamber 215 may have a square or rectangular footprint, and be reached by the microchannels 213, 214 at opposite sides along the Y direction. However, the disclosure is not limited thereto. For example, the footprint of the circulation chamber 215 may be circular, pentagonal, hexagonal, or any other regular or irregular polygonal shape. Also, the microchannels 213, 214 may reach the culture chamber 215 along different directions. For example, one of the microchannels 213, 214 may reach the culture chamber 215 from the Y direction, and the other microchannel 213, 214 may reach the culture chamber 215 from the X direction.

In some embodiments, the region 203 has a thickness T7 which is smaller than the thickness T5 of the region 201 by the depth D2. The depth D2 is larger than the depth D1, so that the thickness T7 is also smaller than the thickness T6. In some embodiments, the regions 202 of depth T6 are disposed between the microchannels 211, 212 and the region 203 of thickness T7. In some embodiments, one or more regions 204 of gradually decreasing thickness may be formed within the region 203, resulting in one or more micro-wells 216 opening in the culture chamber 215. The region 203 of thickness T7 may surround the region(s) 204 of decreasing thickness. The thickness of the region(s) 204 may gradually decrease from the thickness T7 of the region 203 to a minimum thickness T8 reached in correspondence of the bottom of the micro-well(s) 216. That is, the bottom of the micro-well(s) 216 may be separated from the top surface 100t of the sensing chip 100 by a depth D3 along the Z direction. The depth D3 is greater than the depth D2. In some embodiments, the micro-well 216 opens on side of the culture chamber 215 directly facing the top surface 100t of the sensing chip. That is, the micro-well 216 may reach the culture chamber 215 from the Z direction. As illustrated in FIG. 6, the regions 201, 202, 203, 204 of differing thickness (T5-T8) of the channel module 200 all contact the cover module 500, while only the region 201 of thickness T5 contacts the sensing chip 100. In the other regions 202, 203, 204, the bottom surface 200b is separated from the top surface 100t of the sensing chip 100 by the microtrenches forming the microchannels 213, 214, and the recesses forming the culture chamber 215 and the micro-well(s) 216. That is, the top surface 200t of the channel module 200 may be substantially flat. In some embodiments, the top surface 200t of the channel module 200 may be considered a distal surface of the channel module 200 with respect to the sensing chip 100.

In some embodiments, the microchannel 213 extends for the length L6 from the end of the microchannel 211 to the culture chamber 215. Similarly, the microchannel 214 extends for the length L7 from the culture chamber 215 to the end of the microchannel 212. In some embodiments, the culture chamber 215 extends for a length L8 along the Y direction and for a width W5 along the X direction. In some embodiments, the width W5 of the culture chamber 215 may be up to two thirds (⅔) of the width W4 of the channel module 200 along the X direction. In some embodiments, the sum of the lengths L6, L7, and L8 may be up to 80% of the length L5 of the channel module along the Y direction. In some embodiments, the sum of the lengths L6, L7, L8 may be considered as the distance along the Y direction from the end of the microchannel 211 to the end of the microchannel 212. When the microchannels 213, 214 are bent, (i.e., include sections elongated along the X direction and sections elongated along the Y direction), such distance corresponds to the projection along the Y direction of the respective recesses (without counting twice possible overlapping projections). In some embodiments, the culture chamber 215 has a width W5 along the X direction which can be up to 90% of the width W4 of the channel module 200. In some embodiments, the micro-well 216 has a maximum length L9 along the Y direction. In some embodiments, a ratio between the maximum length L9 of the micro-well 216 to the length L8 of the culture chamber 215 may be in the range from ¹⁄₂₅ to ⅕. Similarly, a ratio between the maximum width W6 of the micro-well 216 along the X direction to the width W5 of the culture chamber may be in the range from ¹⁄₁₅ to ⅓.

In some embodiments, the channel module 200 may be accommodated in the recess 530 of the cover module 500 together with the sensing chip 100. That is, the channel module 200 may contact the cover module 500 in the region 520 of thickness T2, while the region 510 of thickness T1 of the cover module 500 may reach the circuit substrate 300 outside the footprint of the sensing chip 100. As illustrated in FIG. 6, the microchannels 211 and 212 may respectively open in correspondence of the through holes 541 and 542 of the cover module 500. That is, the microchannels 211 and 212 are in fluidic communication with the through holes 541 and 542. In some embodiments, a width D4 of the microchannels 211, 212 may be smaller than width D5 of the through holes 541, 542, where the widths D4 and D5 are measured along the same direction (e.g., the Y direction). In some embodiments, the width D4 may be measured at the top surface 200t of the channel module 200, and the width D5 may be measured at the bottom surface 520b of the region 520 of the cover module 500. In some embodiments, the width D4 may correspond to a diameter of the outline of the microchannels 211, 212 at the top surface 200t of the channel module 200, when the microchannels 211, 212 have a circular shape. In some embodiments, the width D4 may correspond to a diagonal of the outline when the microchannels 211, 212 have a square or rectangular shape, and so on. Similar considerations apply to the width D5 with respect to the shape of the through holes 541, 542. In some embodiments, the width D4 is smaller than the width D5. For example the width D4 may be about ⅕ to ½ of the width D5. In some embodiments, the width D4 may be about half of the width D5. In some embodiments, the shapes of the outlines of the microchannels 211, 212 may differ with respect to each other and with respect to the shapes of the outlines of the through holes 541, 542. In FIG. 7 are illustrated the outlines of the through holes 541, 542 at the level height along the Z direction of the bottom surface 520b, where the cover module 500 contacts the channel module 200.

Figure 8:
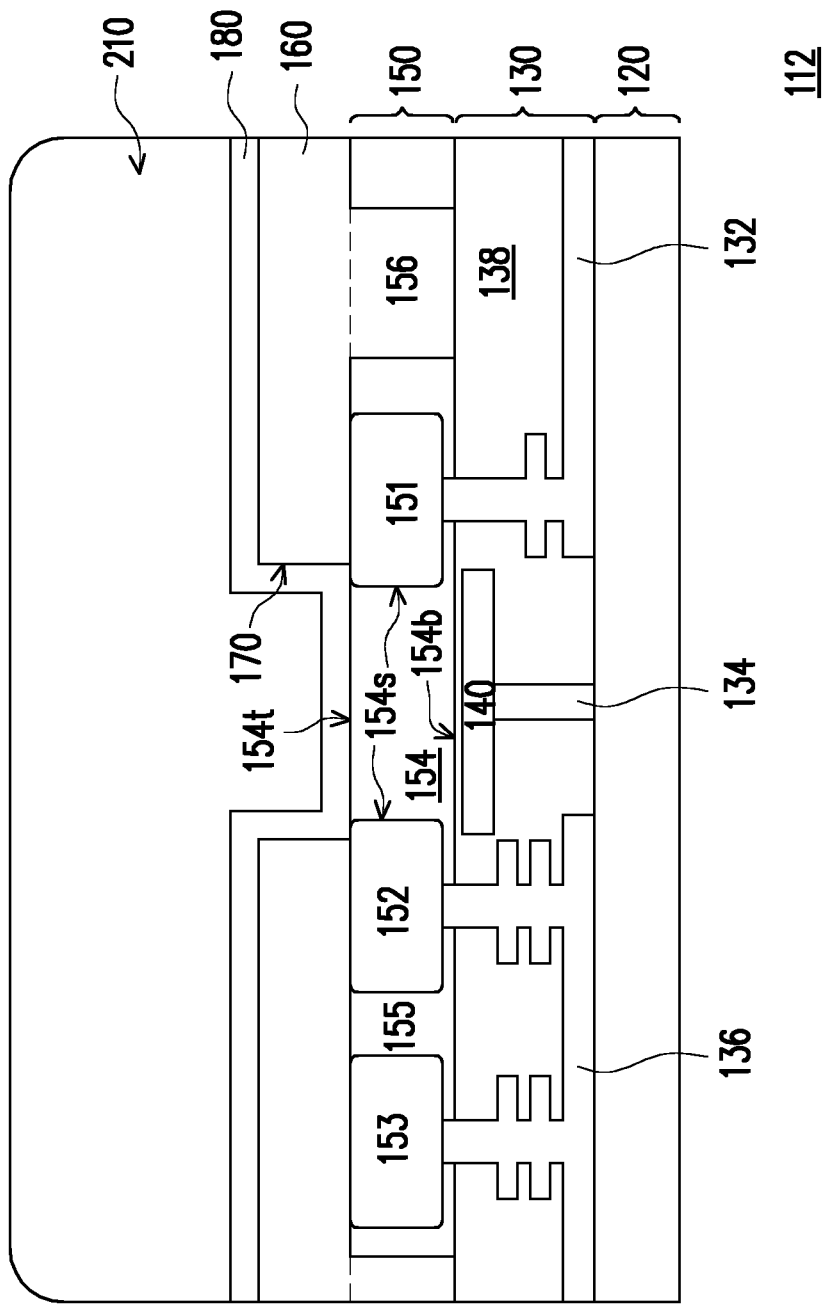
FIG. 8 is a schematic cross-sectional view of a sensing area of a sensing chip of the cell monitoring apparatus according to some embodiments of the disclosure.

Referring to FIG. 6, the sensing chip 100 may have a substrate 110 including semiconductor materials, and having active devices and, optionally, passive devices formed therein. A sensing region 112 may be formed in the substrate 110 at the top surface 100t of the sensing chip 100, in correspondence of the micro-well 216 of the microfluidic channel 210. In some embodiments, the sensing region 112 may extend as much as the micro-well 216, and the micro-well 216 may directly face the sensing region 112. In some embodiments, the sensing region 112 may further extend as much as the culture chamber 215. FIG. 8 is a schematic cross-sectional view of the sensing region 112 of the sensing chip 100 according to some embodiments of the disclosure. The sensing region 112 may be formed in a portion of the substrate 110. The sensing region 112 may include a handling substrate layer 120 which may include a same material as the substrate 110.

A metal interconnect layer 130 may be located on the handling substrate layer 120. The metal interconnect layer 130 includes conductive traces 132, 134, 136 embedded in a dielectric layer 138. While the dielectric layer 138 is illustrated as a single layer, the dielectric layer 138 may be a composite layer. That is, in the metal interconnect layer 130 the conductive traces 132, 134, 136 may be part of one or more metallization tiers, and each metallization tier may be disposed in between a pair of adjacent dielectric layers of the dielectric layer 138. A back-gate 140 may be embedded in the interconnection layer 130, and be electrically connected to at least one of the conductive traces of the metal interconnect layer 130 (e.g., the conductive trace 134). In some embodiments, the back-gate 140 is a polysilicon gate, but the disclosure is not limited thereto.

In some embodiments, a channel layer 150 is disposed on the metal interconnect layer 130. The channel layer 150 includes multiple regions 151-155 of semiconductor material. The semiconductor material of the regions 151-155 may differ in terms of type and concentrations of dopant included. For example, the regions 151, 152, 153 may include strained semiconductor materials (e.g., SiGe), as well as p-type or n-type dopants, and the regions 154, 155 may include a different semiconductor material (e.g., Si), possibly with a different concentration of dopants. In some alternative embodiments, the regions 151-155 may include the same semiconductor material, and may differ from each other, for example, for including dopants of different types and/or at different concentrations. In some embodiments, the regions 151, 152 may act as source and drain regions of a transistor, and the region 153 may act as body for the transistor. For example, the region 152 may act as a source region and the region 151 may act as a drain region. The region 154, which is interposed between the regions 151 and 152 and is contacted from below by the back-gate 140 may act as a channel region of the transistor. That is, the source and drain regions 151, 152 may be disposed at opposite ends of the channel region 154 and contact the region 154 along a pair of opposite side surfaces 154s. The back-gate 140 may contact the region 154 at the bottom surface 154b. The region 153 may be separated from the region 152 by the region 155. In some embodiments, the conductive trace 136 of the metal interconnect layer 130 may electrically connect the region 152 to the region 153. In some embodiments, isolation structures 156 are also included in the channel layer 150. The isolation structures 156 may include an insulation material, for example an oxide or a nitride, such as silicon oxide.

An insulation layer 160 may be disposed over the channel layer 150, preventing the source and drain regions 151, 152 from being exposed to the culture medium. The insulation layer 160 may include oxide or nitrides, for example silicon oxide. In some embodiments, the insulation layer 160 includes one or more openings 170 in correspondence of the channel region 154. That is, insulation layer 160 may cover the source and drain regions 151, 152, the doped region 153, and the substrate region 155, while leaving exposed the channel region 154. In some embodiments, the isolation structures 156 may include the same material as the insulation layer 160. In some embodiments, the isolation structure 156 and the insulation layer 160 may be formed together during a same process step.

A sensing film 180 may be formed over the insulation layer 160. The sensing film 180 may cover the insulation layer 160, and be conformally disposed within the opening(s) 170. The sensing film 180 may contact the channel region 154 within the opening(s) 170, and act as a front gate for the transistor of the sensing region 112. The sensing film 180 may contact the region 154 at the top surface 154t. The top surface 154t may join the pair of opposite side surfaces 154s contacted by the source and drain regions 151, 152. In some embodiments, the capacitance of the sensing film 180 may vary depending on the presence of target analytes in the culture medium contained in the microfluidic channel 210. As such, the front-gate voltage of the transistor of the sensing region 112 may vary as a function of the presence and/or concentration of target analytes in the culture medium. That is, the sensing chip 112 may operate as a field-effect transistor-based biosensor. It should be noted, that while the sensing region 112 in FIG. 8 was illustrated as having a dual-gate field-effect transistor configuration, the disclosure is not limited thereto. Single gate field-effect transistor, or other configurations of transistor-based sensors (e.g., silicon nanowires, organic field-effect transistors, graphene-based field-effect transistors, or the like) may be applied for the sensing area 112.

FIG. 9A to FIG. 11A illustrate some structures of sensing films 180, 1180, 2180, respectively, according to some embodiments of the disclosure. FIG. 9B to FIG. 11B illustrate schematically a sensing mechanism of the sensing films 180, 1180, 2180 respectively illustrated in FIG. 9A to FIG. 11A. For clarity of illustration, in FIG. 9A to FIG. 11B a portion of the region 154 is also included. That is, the views of FIG. 9A to FIG. 11B may correspond to a portion of the sensing films 180, 1180, 2180 included in the opening(s) 170 of the insulation layer 160 (illustrated in FIG. 8).

Referring to FIG. 9A and FIG. 9B, in some embodiments, the sensing film 180 includes a high-k dielectric layer 182. The high-k dielectric layer 182 may include a high-k dielectric material. For example, a material of the high-k dielectric layer 182 may include a metal oxide, such as $ZrO_2$, $Gd_2O_3$, $HfO_2$, $BaTiO_3$, $Al_2O_3$, $LaO_2$, $TiO_2$, $Ta_2O_5$, $Y_2O_3$, STO, BTO, BaZrO, HfZrO, HfLaO, HfTaO, HfTiO, a combination thereof, or other suitable materials. In some alternative embodiments, the material of the high-k dielectric layer 182 may include a silicate such as HfSiO, HfSiON LaSiO, AlSiO, or a combination thereof. In some embodiments, the material of the high-k dielectric layer 182 includes hafnium oxide. In some embodiments, the high-k dielectric layer 182 may expose at the interface hydroxyl groups (OH) or negatively charged deprotonated hydroxyl groups ($O^-$), which may interact with positively charged species present in the culture medium. In some cases, for example when small cationic species (e.g., $M^+$ or $M^{2+}$, where M is a metal atom such as potassium, calcium, sodium, or a low molecular weight polyatomic species such as an ammonium ion) are the target analyte, the high-k dielectric layer 182 itself may be used as a sensing film 180. In some embodiments, the presence or concentration of the small cationic species may affect the capacitance of the sensing film 180. As the sensing film 180 is used as a front-gate for the transistor of the sensing region 112 (as illustrated, e.g., in FIG. 8), changes in the capacitance of the sensing film 180 may be transformed in an electrical signal, through which the presence and concentration of the target analyte 802 can be detected. In some embodiments, the target analyte 802 serves as an indicator of the metabolic or physiological state of a cell 802 under study. The disclosure is not limited by the type of cells 802 which may be used with the cell monitoring apparatus. Any cell line (e.g., cardiac cells, pancreatic cells, neural cells, skin cells, cancerous cells, stem cells, and so on) may be used, depending on the phenomenon under study.

Figure 10A:
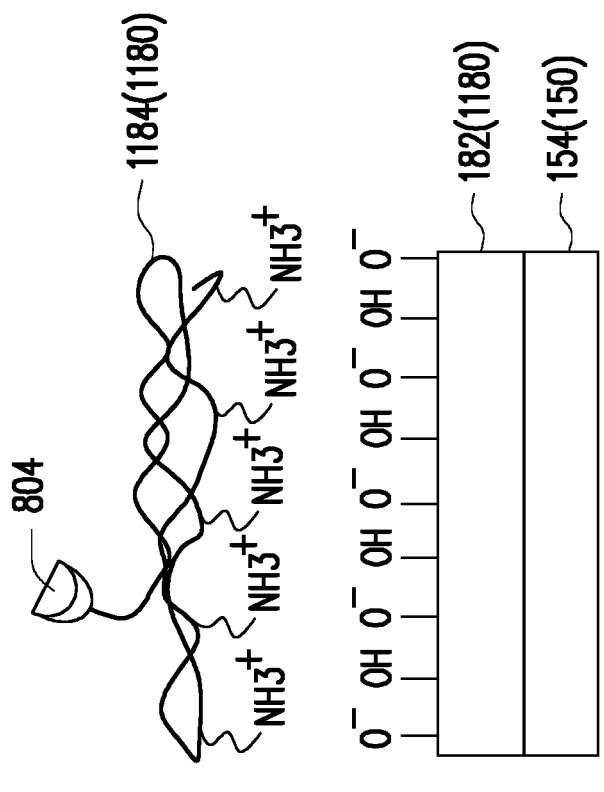
Figure 10B:
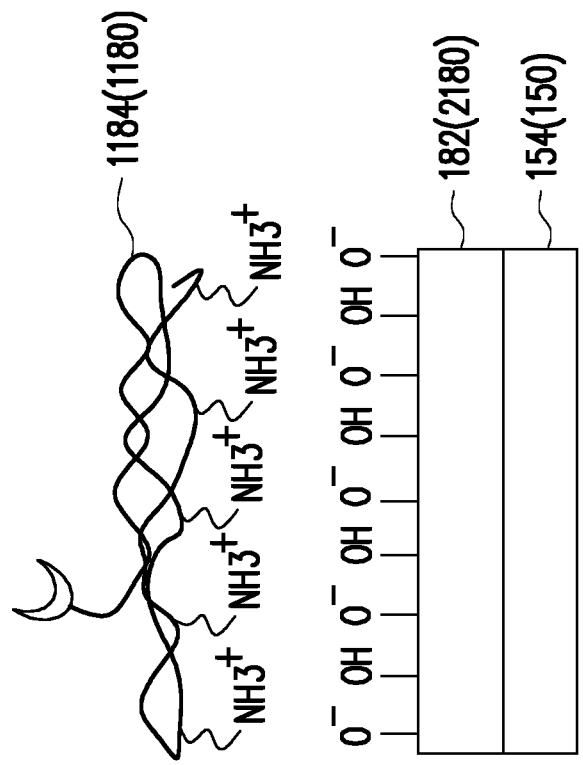
Figures 11A, 11B:
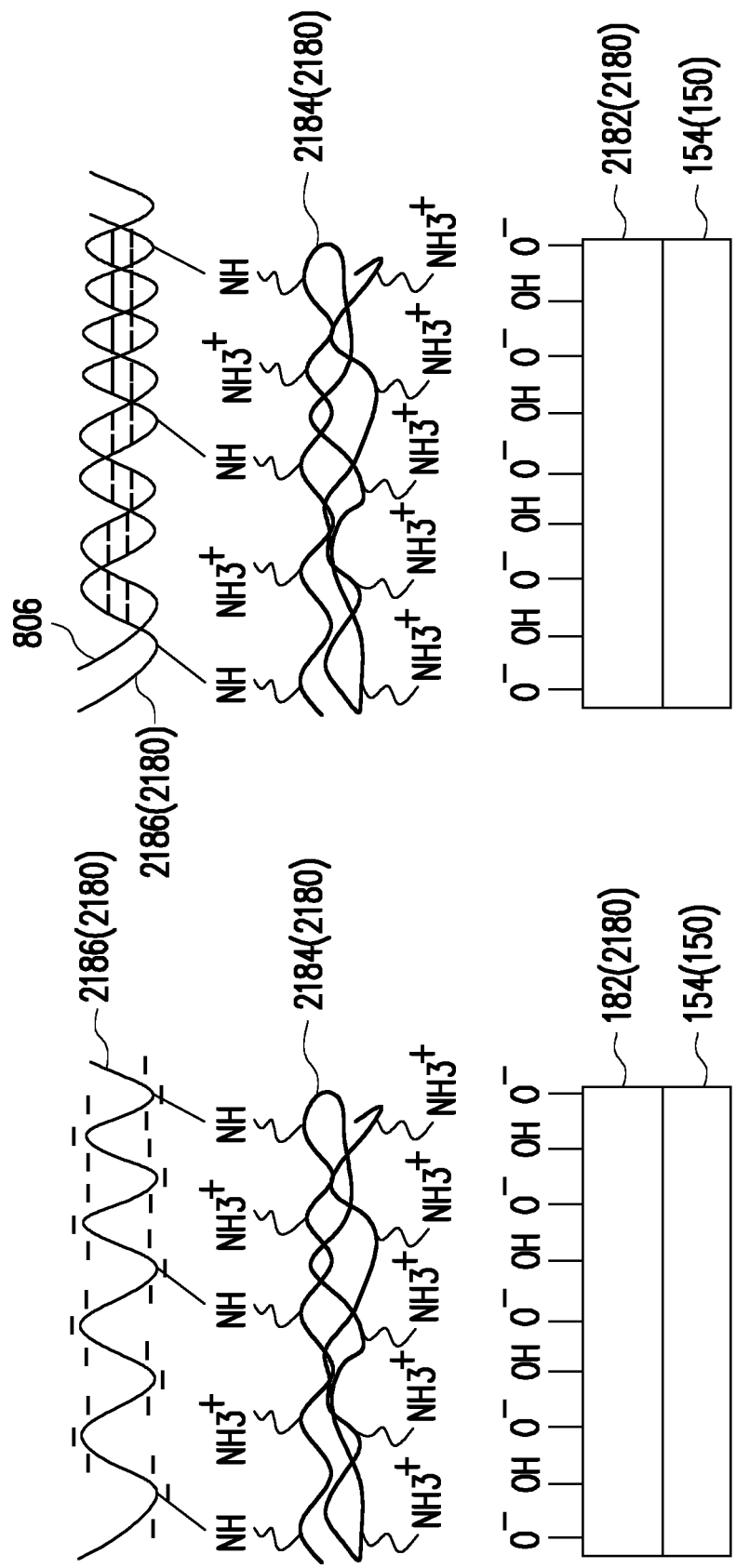

In some alternative embodiments, sensing of more complex analytes may be of interest, or, for example, there may be the necessity of a more specific response. In such cases, the high-k dielectric layer 182 may be functionalized with any one or more bio-probes, as may be available in the field of bio-sensing. For example, as illustrated in FIG. 10A and FIG. 10B, in the sensing film 1180 a positively charged probe 1184 may interact with the negatively charged groups at the interface of the high-k dielectric layer 182 so as to be "anchored" to the high-k dielectric layer 182. In some embodiments, the probe 1184 may have been functionalized to include a positively charged tag, such as a poly-lysine chain. The cationic groups in the positively charged tag (e.g., ammonium groups in a poly-lysine chain, imidazolium groups, and so on) may interact with the (deprotonated) hydroxy groups of the high-k dielectric layer 182 to adsorb the probe 1184 to the high-k dielectric layer 182. For example, salt bridges and hydrogen bonds may be formed between the (deprotonated) hydroxy groups and the positively charged amino-acid residues at the interface of the high-k dielectric layer 182 and the probe 1184. In some embodiments, the probe 1184 may be capable of interacting with target analytes 804 which may be present in the culture medium. Upon interaction of the probe 1184 with the target analyte 804, the capacitance of the sensing film 1180 varies, thus enabling sensing of the target analytes.

In some alternative embodiments, direct functionalization of the probe 1184 with a positively charged tag may not be practical, for example because such functionalization may reduce or annihilate the affinity of the probe 1184 for the target analyte 804. In such cases, as illustrated for the sensing film 2180 in FIG. 11A and FIG. 11B, a probe 2186 may be indirectly adsorbed to the high-k dielectric layer 182 via an anchoring compound 2184. For example, the anchoring compound 2184 may be a polypeptide rich in positively charged aminoacidic residues (e.g., lysines, hystidines, arginines). The positively charged sites on the anchoring compound 2184 may interact, for example via salt bridges and/or hydrogen bonds, with the (deprotonated) hydroxy groups of the high-k dielectric layer 182, thus "immobilizing" the anchoring compound to the high-k dielectric layer 182. Similarly, a region of the probe 2186 may interact with other sites of the anchoring compound 2184, to become "immobilized" to the high-k dielectric layer 182. For example, the probe 2186 may include multiple negatively charged sites, which may interact with other positively charged sites of the anchoring compound 2184 through salt bridges and/or hydrogen bonds. In some embodiments, depending on the functional groups present in the probe 2186, bonding with the anchoring compound 2184 may also be possible. In some embodiments, the probe 2186 may be absorbed or even bonded to the positively charged anchoring compound 2184, for example by reaction with one of the ammonium groups. For example, the probe 2186 may be a single strand nucleotidic sequence (e.g., ssDNA or ssRNA), negatively charged because of the abundance of phosphate groups, and the target analyte 806 may be the complementary sequence to the probe 2186. In such cases, upon hybridization of the probe 2186 with the complementary sequence of the target analyte 806, the capacitance of the sensing film 2180 may change, thus enabling sensing of the target analyte 806.

It should be noted that while in the description of FIG. 9A to FIG. 11B certain specific types of bio-probes or interactions have been mentioned, the disclosure is not limited thereto. Enzymatic probes, polynucleotidic probes, primary or secondary antibodies, aptameric probes, and other probes which upon binding with the target analyte affect the capacitance of the sensing films 180, 1180, 2180 are all contemplated within the scope of the disclosure, and may be adequately selected according to the nature of the target analyte of interest.

Figure 12A:
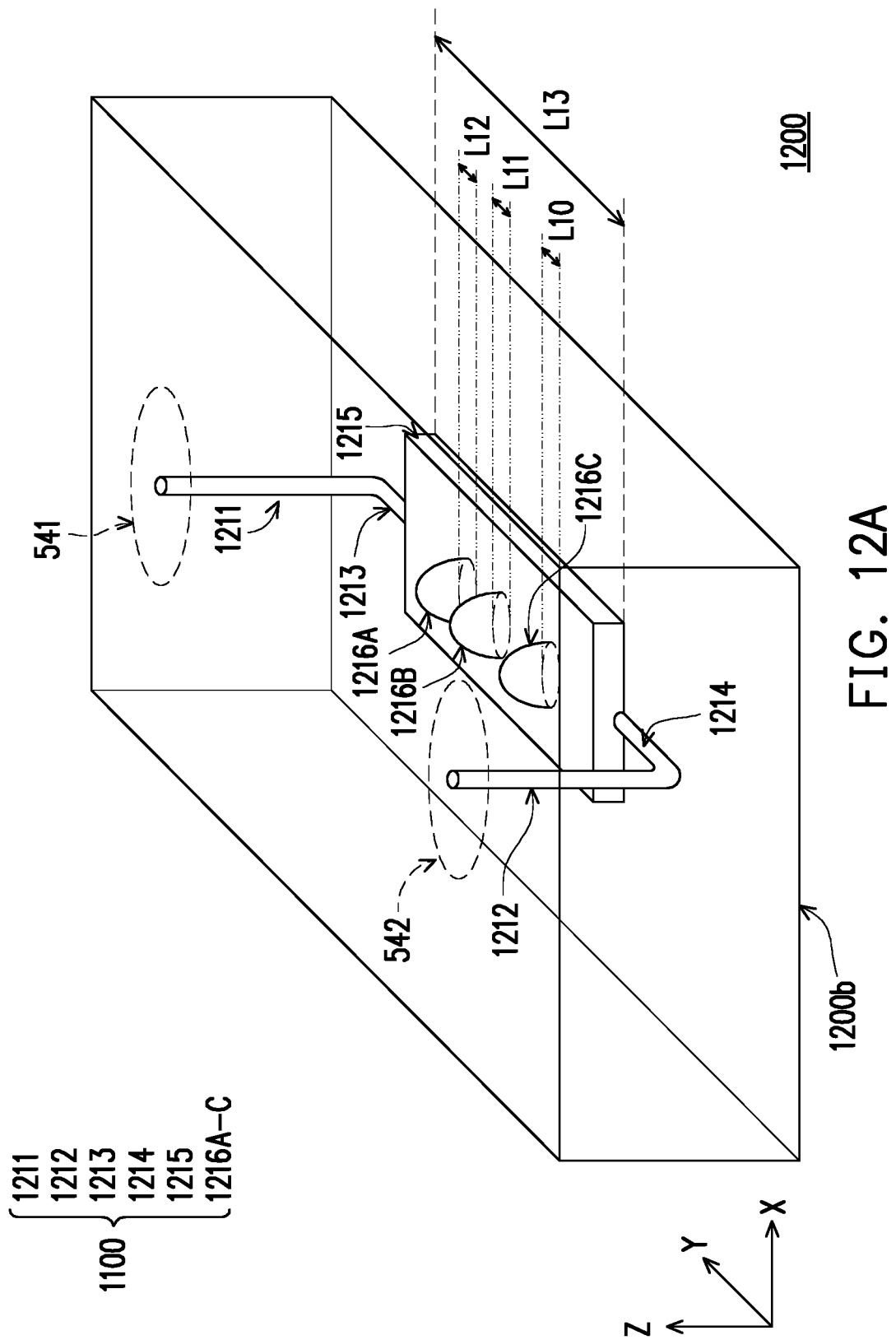
FIG. 12A to FIG. 12C are schematic perspective views of channel modules according to some embodiments of the disclosure.

FIG. 12A is a schematic perspective view of a channel module 1200 according to some embodiments of the disclosure. In some embodiments, the channel module 1200 may have a similar structure to the channel module 200 (illustrated, e.g., in FIG. 7). The channel module 1200 may be used in a cell monitoring apparatus in place of the channel module 200. In some embodiments, the channel module 1200 includes the microchannels 1211, 1212 extending through the channel module 1200 in the thickness direction (e.g., the Z direction). The microchannels 1213 and 1214 are formed by the elongated recesses at the bottom surface 1200b of the channel module 1200, and are connected at the lower ends of the microchannels 1211 and 1212, respectively. The microchannels 1213, 1214 open in the cultivation chamber 1215, similarly to what was previously described for the channel module 200. In some embodiments, multiple micro-wells 1216A-1216C open in the same cultivation chamber 1215, from the same side of the cultivation chamber 1215 (e.g., from the Z direction). For example, FIG. 12A illustrates a line of micro-wells 1216A-1216C opening at the top of the same cultivation chamber 1215. In some embodiments, each micro-well 1216A-1216C may be associated with a dedicated sensing area 112 of the sensing chip 110 (illustrated, e.g., in FIG. 6 and FIG. 8 above). That is, in the channel module 1200 it may be possible to run multiple experiments simultaneously. In some embodiments, the combined extension of the micro-wells 1216A-1216C along the Y direction (e.g., the sum of the lengths L10, L11, and L12) may be up to 80% of the length L13 of the culture chamber 1215 along the Y direction.

Figure 12B:
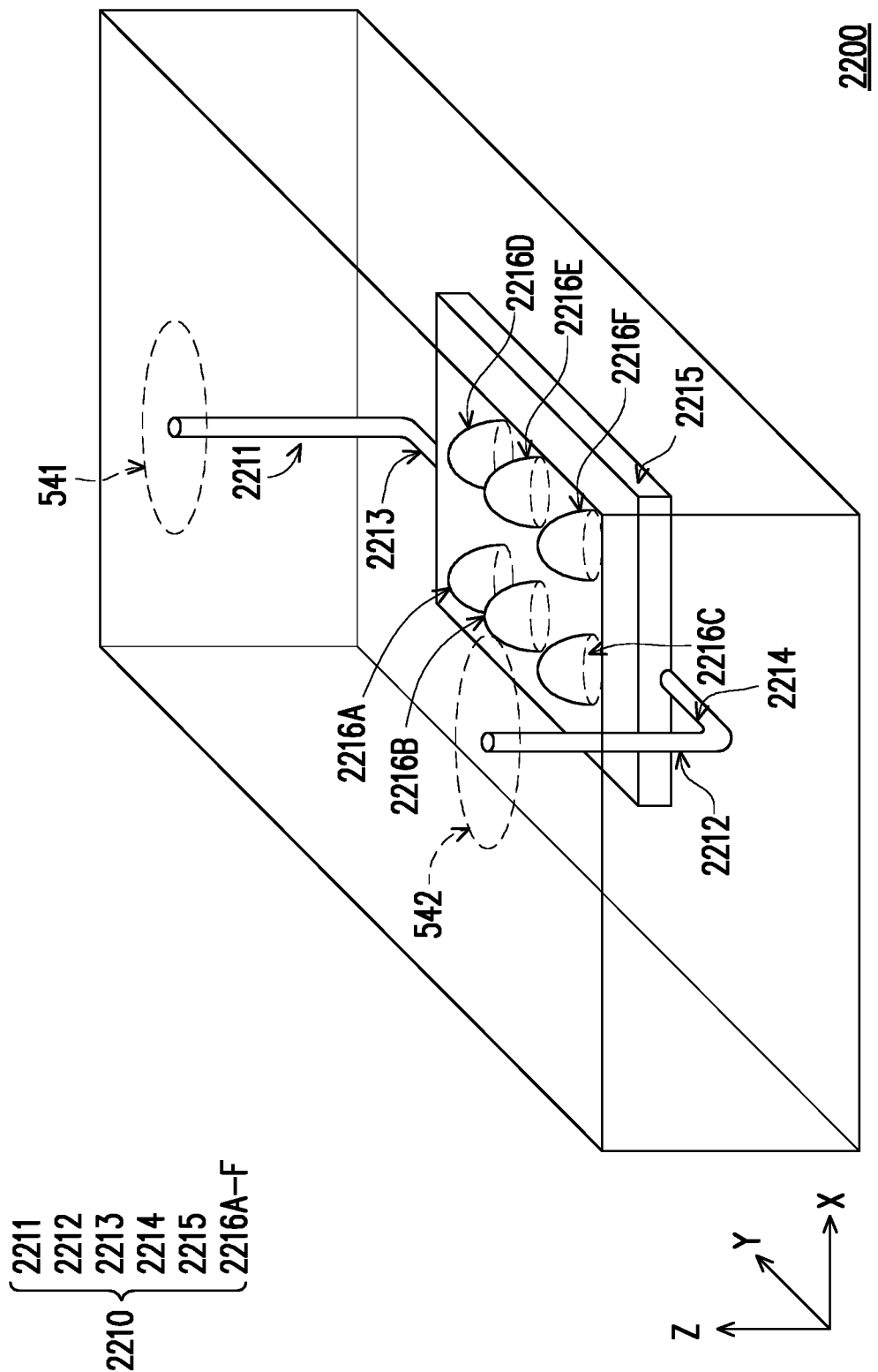
Figure 12C:
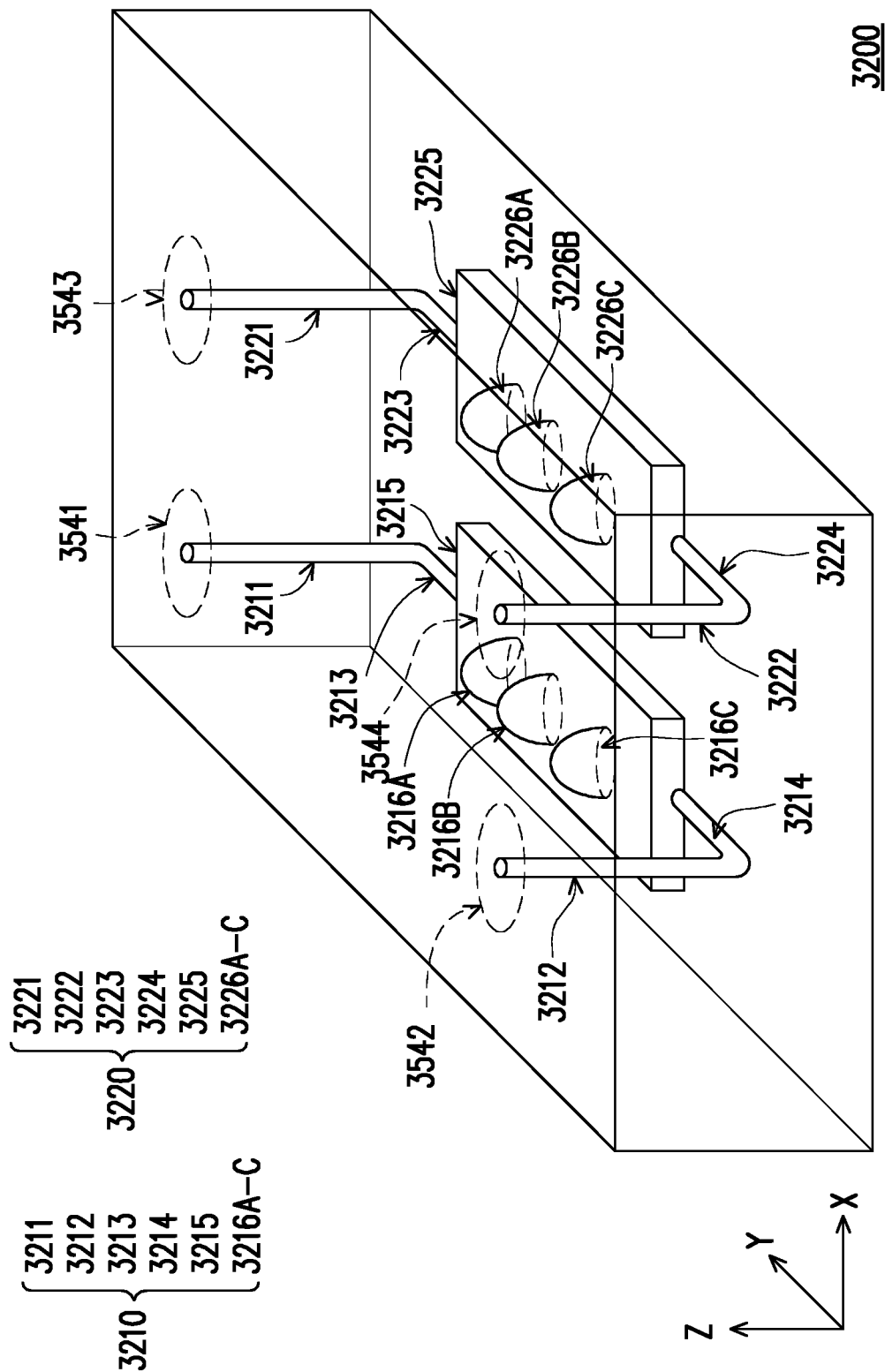

The disclosure is not limited by the number or the arrangement of the micro-wells. For example, while in FIG. 12A the micro-wells 1216A-1216C are disposed in a linear array, in the channel module 2200 of FIG. 12B the micro-wells 2216A-2216F are disposed in a matrix configuration, along multiples rows and columns. Furthermore, the disclosure is not limited by the number of microfluidic channels formed in a channel module. For example, as illustrated in FIG. 12C, the channel module 3200 may include two independent microfluidic channels 3210 and 3220. Each microfluidic channel 3210, 3220 may have the same structure as one of the microfluidic channels disclosed above. For example, in FIG. 12C the microfluidic channels 3210, 3220 are illustrated with structures similar to the microfluidic channel 1210 of the channel module 1200 of FIG. 12A, however other structures for the microfluidic channels 3210, 3220 are also possible, such as the structures of the microfluidic channel 210 of FIG. 7, or of the microfluidic channel 2210 of FIG. 12B. When the channel module 3200 includes multiple microfluidic channels 3210, 3220, the cover module (not illustrated) may include multiple through holes 3541-3544, the outlines of which are illustrated in FIG. 12C. Each through hole 3541-3544 opens in correspondence of one of the microchannels 3211, 3212, 3221, 3222 extending in the thickness direction Z through the channel module 3220. In some embodiments, with the channel module 3200 having multiple independent microfluidic channels 3210, 3220 illustrated in FIG. 12C, it may be possible to run simultaneously test experiments and control experiments. Of course, the disclosure is not limited by the number of microfluidic channels 3210, 3220 included in the channel module 3200.

In some embodiments, the channel modules 200, 1200, 2200, 3200 may be assembled with the corresponding cover modules (e.g., the cover module 500) before running the desired experiments, and may be discarded upon conclusion of the experiments. That is, the channel modules 200, 1200, 2200, 3200 may be considered consumable parts of the cell monitoring apparatus. In some embodiments, the cover module may also be considered a consumable, or may be reused, for example upon substitution of the channel module.

Figure 13:
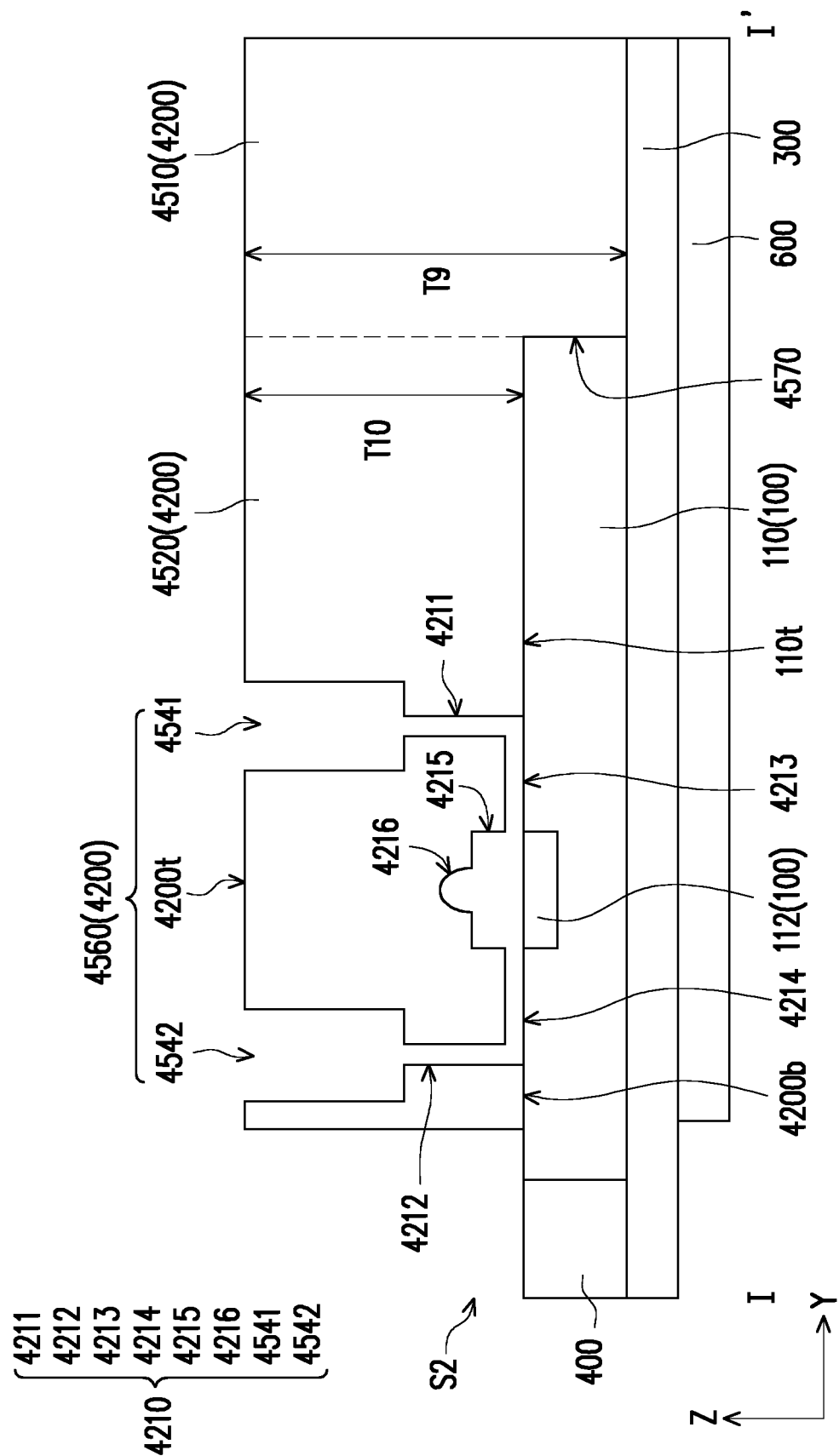
FIG. 13 is a schematic cross-sectional view of a portion of a cell monitoring apparatus according to some embodiments of the disclosure.

In FIG. 13 is illustrated a schematic cross-sectional view of a portion of a cell monitoring apparatus S2 according to some embodiments of the disclosure. The cross-sectional view of FIG. 13 is illustrated in a YZ plane corresponding to the plane of view of FIG. 6. In the cell monitoring apparatus S2, the channel module 4200 includes a region 4510 of thickness T9, a region 4520 of thickness T10, and a region 4560 of variable thickness in which the recesses constituting the microfluidic channel 4210 are formed. The thickness T10 and the thickness T9 are both measured along the Z direction (e.g., vertical with respect to the top surface 110$t$ of the sensing chip 100), and the thickness T10 is greater than the thickness T9. When the cell monitoring apparatus S2 is assembled, the region 4510 may contact the carrier substrate 300, and the region 4520 may contact the top surface of the sensing chip 100. The region 4560 also extends over the sensing chip 110, overlies the sensing area 112, and may contact at the periphery of the microfluidic channel 4210 the top surface 110$t$, so as to prevent the culture medium to spread all over the top surface 110$t$. As such, the regions 4510, 4520, 4560 of the channel module 4200 may define a recess 4570 in which the sensing chip 100 is at least partially accommodated. In the region 4560 of variable thickness, channels and recesses are formed so that the microfluidic channel 4210 is formed between the channel module 4200 (particularly, its bottom surface 4200$b$) and the top surface 100$t$ of the sensing chip 100. The region 4560 may include inlet and outlet tanks 4541, 4542 formed at the top surface 4200$t$ of the channel module 4200 and penetrating in the channel module 4200 for only part of the thickness T10. Microchannels 4211, 4212 may depart from the inlet and outlet tanks 4541, 4542 to extend through the remaining portion of the thickness T10, to reach the bottom surface 4200$b$ of the channel module 4200 on top of the sensing chip 100. Recesses on the bottom surface 4200$b$ may then form the microchannels 4213, 4214, the culture chamber 4215 and the micro-well(s) 4216, similarly to what was previously described for the channel modules 200, 1200, 2200, 3200 with respect to FIG. 7 and FIG. 12A to FIG. 12C. Other aspects and relative dimensions of the microfluidic channel 4210 may be similar to what was previously discussed with reference to the microfluidic channel 210 (illustrated, e.g., in FIG. 6 and FIG. 7).

Figure 14:
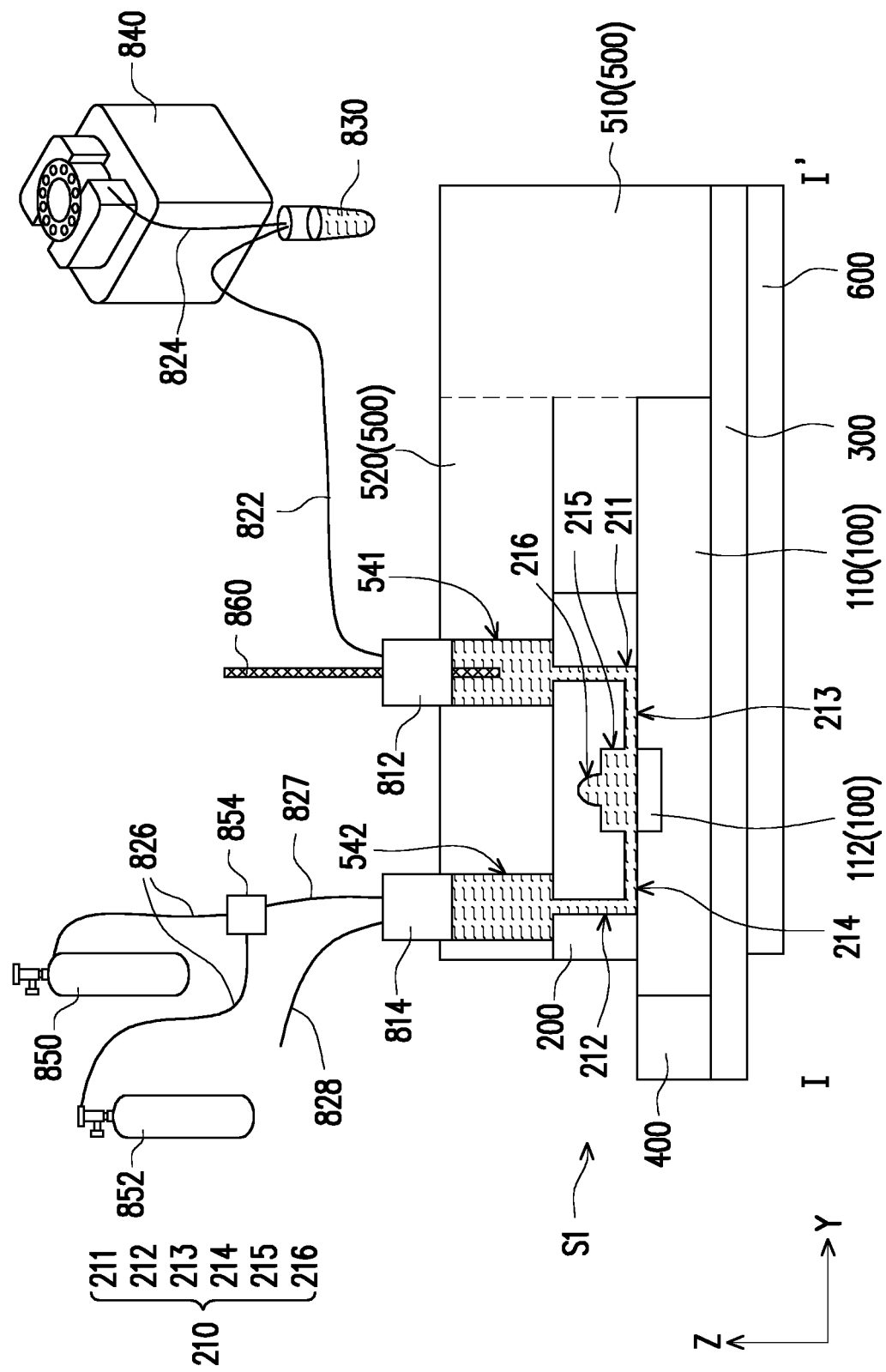
FIG. 14 is a schematic cross-sectional view of a cell monitoring apparatus connected to a medium circulation system according to some embodiments of the disclosure.

FIG. 14 is a schematic cross-sectional view of the cell monitoring apparatus S1 connected to a medium circulation system according to some embodiments of the disclosure. The view of FIG. 14 for the cell monitoring apparatus S1 is taken in a YZ plane corresponding to the plane of view of FIG. 6. As illustrated in FIG. 14, in some embodiments, the cell monitoring apparatus S1 is connected to a medium circulation system to allow circulation of a culture medium within the microfluidic channel 210. In some embodiments, connectors 812, 814 may be disposed in the through holes 541, 542 of the cover module 500, at the opposite end with respect to the channel module 200. In some embodiments, the connectors 812, 814 may be valves to regulate fluidic flow, and prevent spillages. In some embodiments, one of the connectors (e.g., the connector 812) is used as inlet for a fluid medium, and the other connector (e.g., the connector 814) is used as an outlet for the fluid medium. In some embodiments, the connector used as an inlet connector (e.g., the connector 812) may be part of a more complex fluid inlet system, which may, for example, include mixing chambers (not shown), bubble traps (not shown), filters, and the like. In some embodiments, one or more sections of tubing 822, 824, connect the inlet connector 812 to a medium reservoir 830 and a fluid pump 840. For example, culture medium contained in the medium reservoir 830 is pumped by the fluid pump 840 through the tubing 822, 824 towards the connector 812. However, the disclosure is not limited to the use of pumps. For example, is some embodiments the culture medium may be introduced in the cell monitoring apparatus S1 by pipetting.

In some embodiments, one of the connectors 812 or 814 may be connected to one or more gas cylinder 850, 852 (e.g., $CO_2$, $O_2$, or the like) to regulate the concentration of gases in the culture medium according to the requirements of the cellular lines under study. For example, as illustrated in FIG. 14, two gas cylinders 850, 852 are connected by tubing 826 to a gas regulator 854, and the outflow of the gas regulator 854 may reach the connector 814 through the tubing 827. In some embodiments, a $CO_2$ cylinder (e.g., the gas cylinder 850) and an $O_2$ cylinder (e.g., the gas cylinder 852) may be connected to the gas regulator 854 so as to deliver a gas mixture adequate to cultivate of the cells, for example a 95:5 (v/v) mixture of $O_2$ and $CO_2$. In some embodiments, a reference electrode 860 may be inserted in one of the through holes 541 or 542, for example through the corresponding connectors 812 or 814. The reference electrode 860 may be connected to the sensing chip 100, and may be used as reference electrode for the transistor of the sensing area 112.

During use, culture medium may be introduced in the cell monitoring apparatus S1. For example, the culture medium may enter the cell monitoring apparatus S1 through the connector 812, filling the through hole 541 which is used as inlet tank. From the through hole (inlet tank) 541, the culture medium may reach the top surface 110$t$ of the sensing chip 100 through the microchannel 211. At the end of the microchannel 211, the culture medium may flow on the top surface 110$t$ of the sensing chip 100 towards the culture chamber 215 through the microchannel 213. The culture medium may fill the culture chamber 215 and the micro-well 216, and further flow towards the microchannel 212 through the microchannel 214. From the microchannel 214, the culture medium may reach the through hole 542, which would then act as outlet tank for the cell monitoring apparatus S1. The culture medium would then leave the cell monitoring apparatus S1 through the connector 814, proceeding through the tubing 828 to a waste collection container (not shown) or back to the medium reservoir 830, depending on whether it is recycled or not. In some embodiments, when multiple experiments are run simultaneously (for example, with the channel module 3200 of FIG. 12C), the cell monitoring apparatus may be connected to multiple independent medium circulation systems, according to the requirements of the experiment performed. Similarly, the inlet connector 812 may include additional tubing (not shown) to allow introduction of reactants at desired times (e.g., without adding the reactants in the culture medium contained in the medium reservoir 830).

Figure 15A:
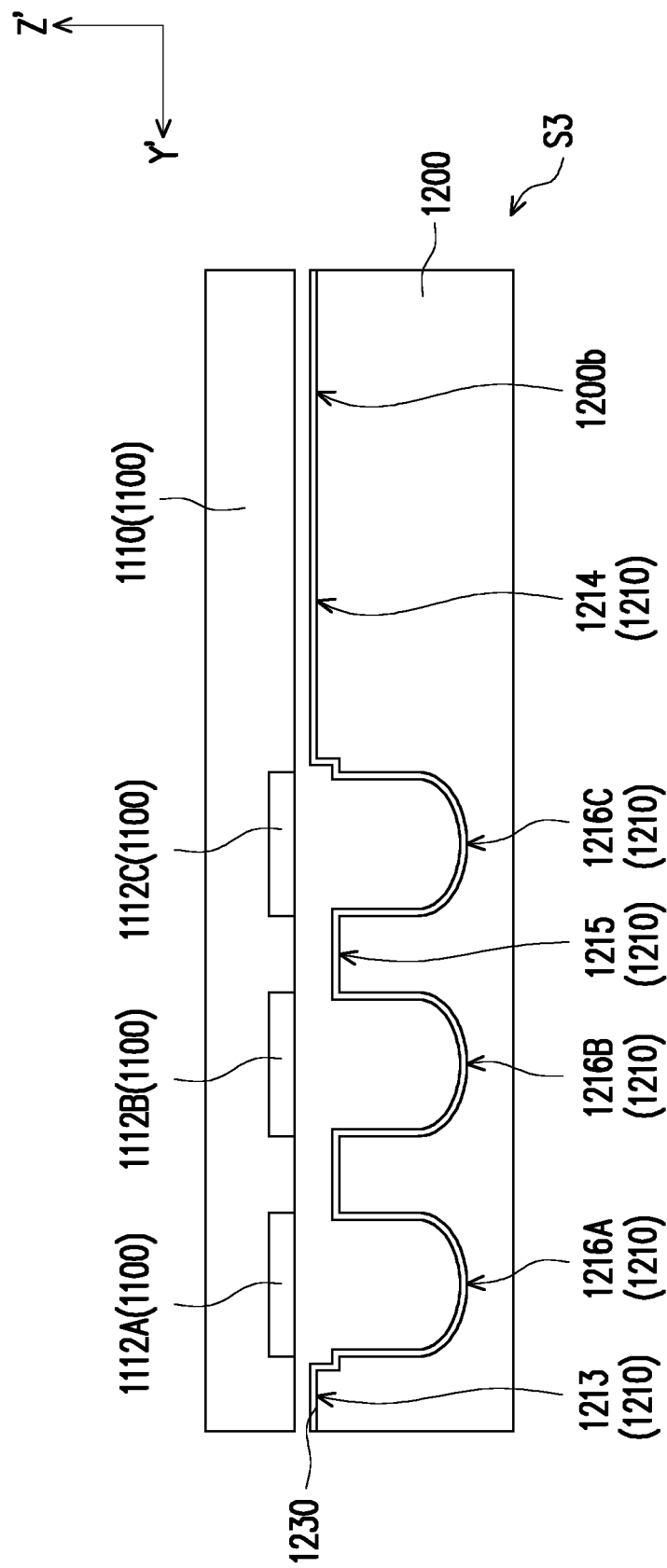
FIG. 15A to FIG. 15D are schematic cross-sectional views of some steps performed during use of a cell monitoring apparatus according to some embodiments of the disclosure.

FIG. 15A to FIG. 15D are schematic views of a cell monitoring apparatus S3 in use according to some embodiments of the disclosure. In FIG. 15A to FIG. 15D are illustrated the axis Y' and Z' of a coordinate system of a reference frame for the cell monitoring apparatus S3, for example the coordinate system of a laboratory (not shown) in which the cell monitoring apparatus S3 may be used. The positive Z' direction may point towards the ceiling of the laboratory (i.e., gravity would be expected to pull towards the negative Z' direction). FIG. 16 is a schematic flow-chart illustrating a method of using a cell monitoring apparatus according to some embodiments of the disclosure. In some embodiments, the cell monitoring apparatus S3 is assembled (step P10). In some embodiments, assembling the cell monitoring apparatus S3 includes disposing the channel module 1200 on the sensing chip 1100, with the bottom surface 1200b of the channel module directly facing the sensing chip 1100. The cell monitoring apparatus S3 includes the sensing chip 1100 and the channel module 1200 of FIG. 12A for illustration purpose, however, similar methods of use can be applied with the other channel modules (e.g., 200, 2200, 3200, 4200) disclosed. As illustrated in FIG. 15A, the sensing chip 1100 may include a dedicated sensing area 1112A-1112C for each of the micro-wells 1216A-1216C of the channel module 1200. Each sensing area 1112A-1112C may be configured as described above with reference to FIG. 8 to FIG. 11B. In some embodiments, an anti-adhesion layer 1230 may be disposed on the bottom surface 1200b of the channel module 1200 within the microfluidic channel 1210. The anti-adhesion layer 1230 may include a material that prevents adhesion of cells to the surfaces of the channel module 1200. In some embodiments, the anti-adhesion layer 1230 includes highly hydrophilic materials. For example, the anti-adhesion layer 1230 may include hydrophilic proteins such as albumin, or hydrophilic polymeric compounds such as polyhydroxyethyl methacrylate, polyethylene glycol, 2-methacryloyloxyethylphosphorylcholine, or the like. In some embodiments, the anti-adhesion layer 1230 may include polyethylene glycol.

In some embodiments, assembling the cell monitoring apparatus S3 may also include disposing the sensing chip 1100 with the carrier substrate 300 on the base module (e.g., the base module 600 illustrated in FIG. 1) before disposing the channel module 1200 on the sensing chip 1100. Furthermore, assembling the cell monitoring apparatus S3 may also include disposing the cover module (e.g., the cover module 500 illustrated in FIG. 1) on the channel module 1200, and fastening the cover module to the base module. However, the disclosure is not limited thereto. In some alternative embodiments, the cell monitoring apparatus S3 may be provided pre-assembled, so that the step P10 does not need to be performed. In some embodiments, the cell monitoring apparatus S3 may then be connected to any external equipment which may be required by the experimental protocol (as illustrated, e.g., in FIG. 14).

Figure 15B:
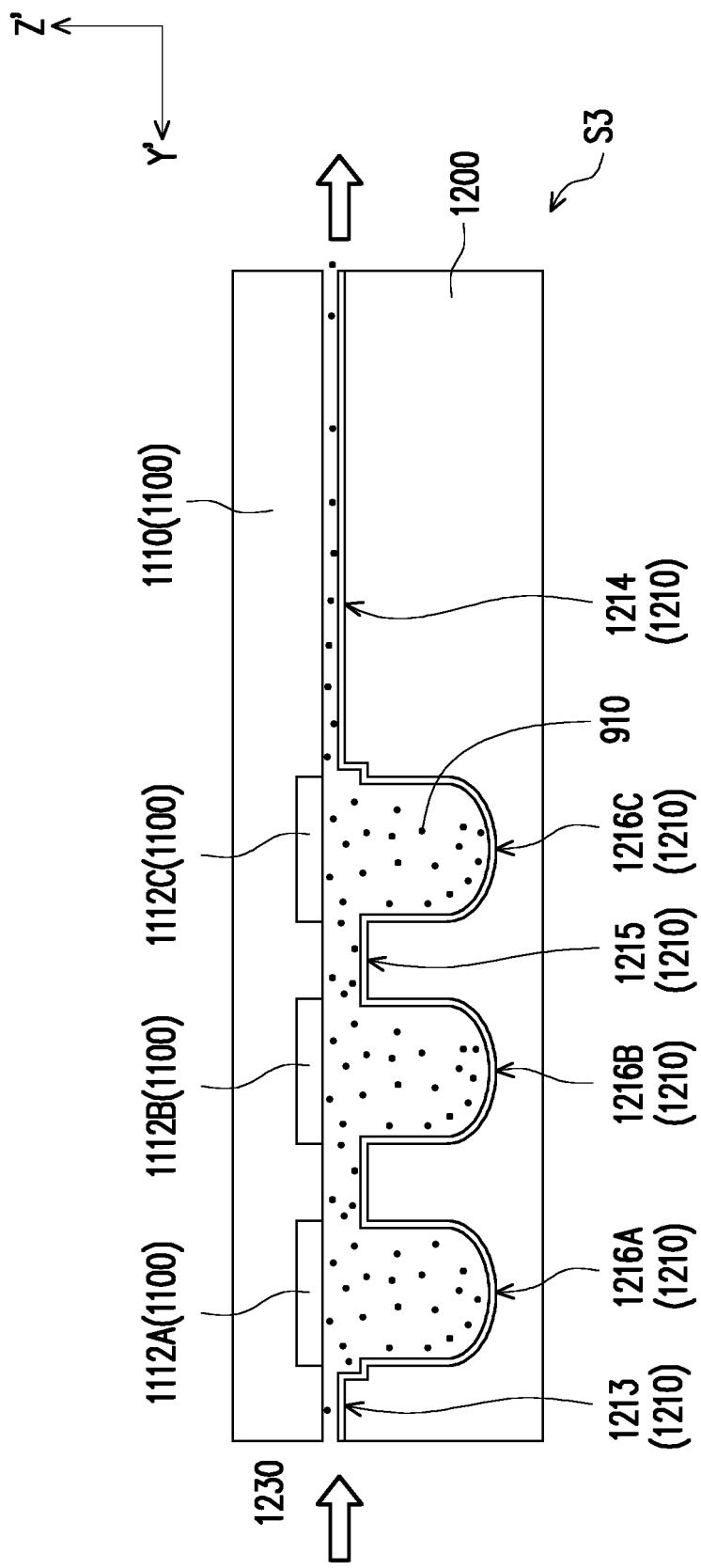
Figure 16:
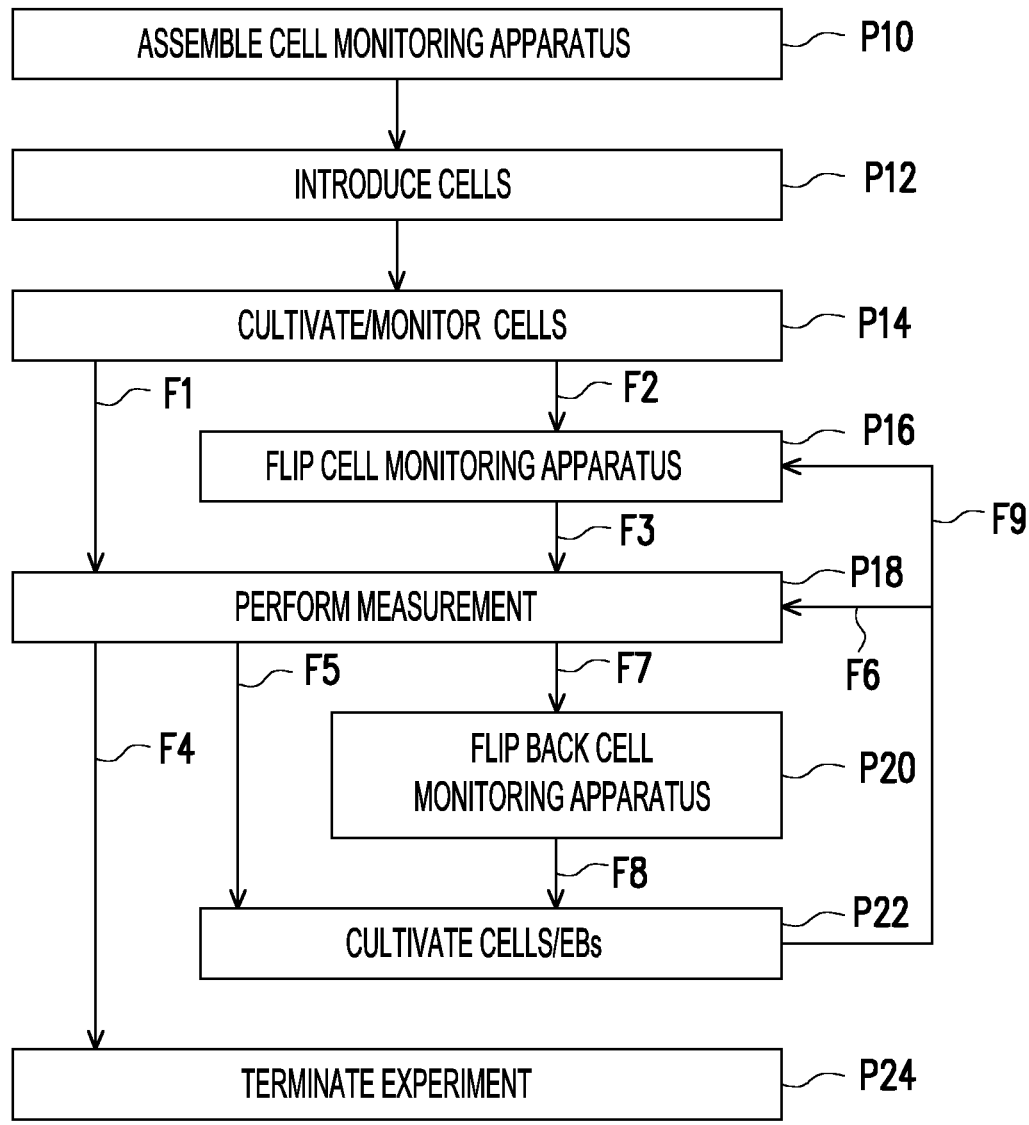
FIG. 16 is a schematic flow-chart of a cell monitoring method according to some embodiments of the disclosure.

Referring to FIG. 15B and to FIG. 16, a culture medium including suspended cells 910 may be introduced in the microfluidic channel 1210 (step P12), for example through the microchannel 1211 (illustrated, e.g., in FIG. 12A). Through the microchannel 1213, the culture medium with the suspended cells 910 may reach the culture chamber 1215 and the micro-wells 1216A-1216C. The suspended cells 910 may then be cultured within the culture chamber 1215 and the micro-wells 1216A-1216C for a time as long as it is required by the experimental protocol (step P14). During the culturing time, fresh medium with nutrients may be introduced as needed. By action of gravity, the cells 910 may accumulate within the micro-wells 1216A-1216C, for example towards the bottoms of the micro-wells 1216A-1216C. During the culturing time, the sensing area 1112A-1112C of the sensing chip 1100 may be used to monitor the physiological state of the cells, for example by determining the pH of the culture medium or the presence in the medium of markers which may be released by the cells 910.

Furthermore, the anti-adhesion layer 1230 may prevent the cells 910 from attaching to the channel module 1200. Rather, referring to FIG. 15B, FIG. 15C, and FIG. 16, the suspended cells 910 may aggregate with each other to form three-dimensional aggregates 920. In some embodiments, the three-dimensional aggregates 920 may be spheroids, in which the individual cells 910 experience an environment which is closer to physiologically relevant conditions than the original suspended state. That is, in the three-dimensional aggregates 920, the cells 910 may exist in a tissue-like environment, allowing study of responses in conditions that are physiologically closer to in vivo studies. In some embodiments, the micro-wells 1216A-1216C may be formed by hemispherical recesses. The hemispherical shape of the micro-wells 1216A-1216C may result in a culture space similar to the conditions encountered when three-dimensional aggregates are formed with the method of the hanging droplets.

In some embodiments, once the cells 910 have aggregated in the three-dimensional aggregates 920, responses to environmental stimuli may be investigated (step P18, process flow F1), for example by detecting the presence of bio-markers at the sensing areas 1112A-1112C through one of the sensing mechanisms described above with reference to FIG. 9A to FIG. 11B. For example, the micro-physiological state of aggregated cardiac cells may be monitored by assessing the extracellular release of potassium, sodium, or calcium ions. Similarly, the extracellular release of other bio-markers may be detected by selecting appropriate sensing films 180, 1180, or 2180, for example.

Figure 15C:
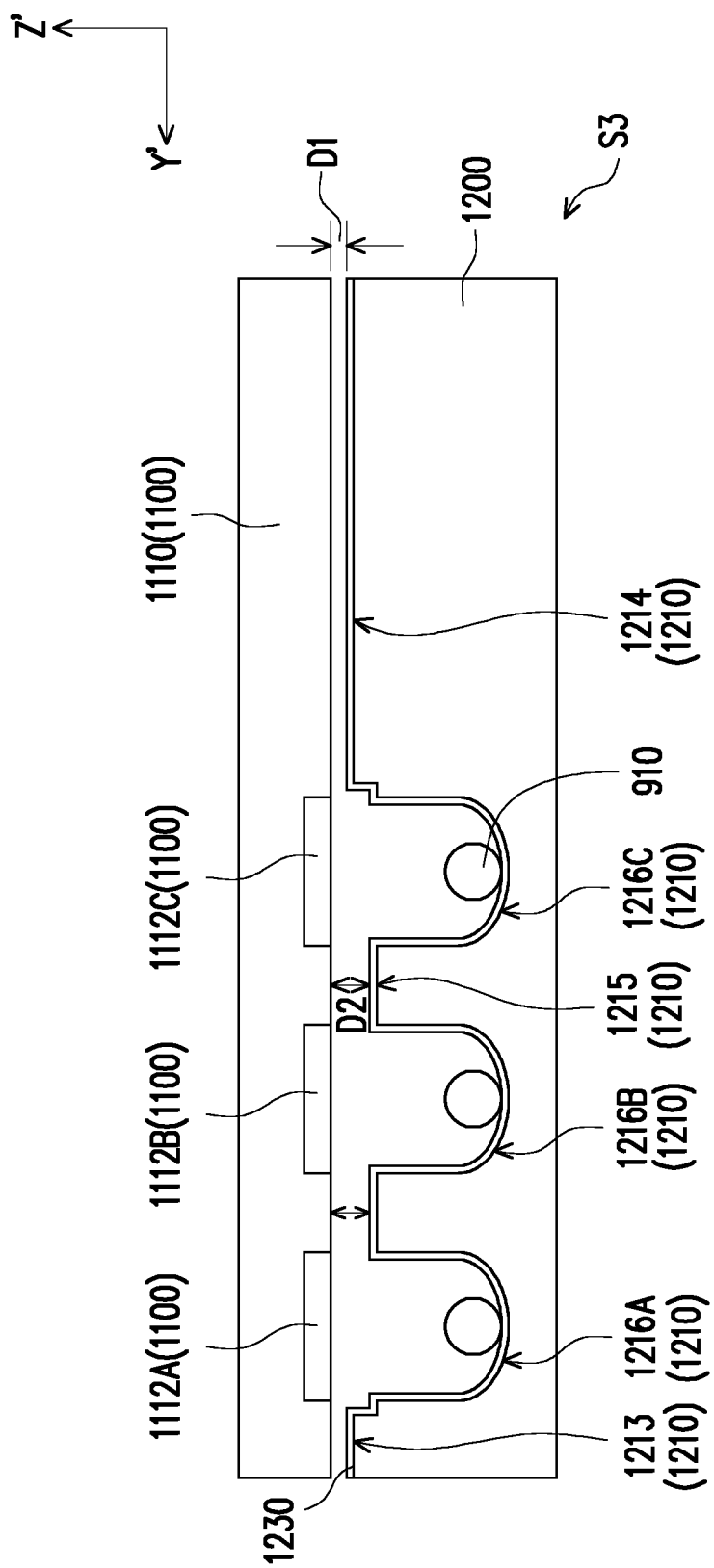
Figure 15D:
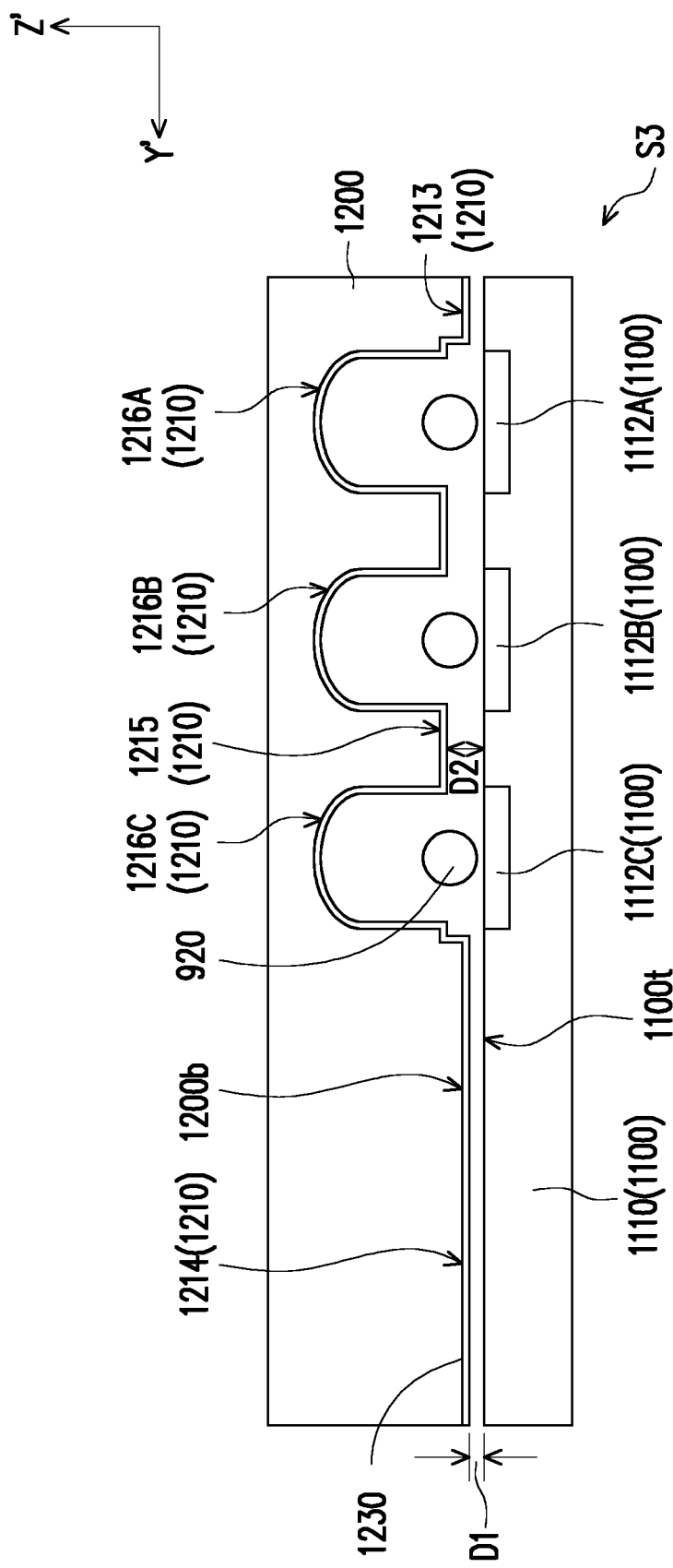

In some embodiments, the data acquisition step P18 may be performed with the cell monitoring apparatus S3 in the conditions as illustrated in FIG. 15C (process flow F1). However, the disclosure is not limited thereto. Referring to FIG. 15C, FIG. 15D and FIG. 16, in some embodiments, the sensitivity and specificity of the measured response between different micro-wells 1216A-1216C may be increased by overturning (flipping upside-down) the cell monitoring apparatus S3 (step P16, process flow F2), so that the three-dimensional aggregates 920 may leave the bottom of the micro-wells 1216A-1216C and move closer to the sensing areas 1112A-1112C before or during acquisition of the experimental data (step P18, process flow F3).

In some embodiments, after acquisition of data, the experiment may terminate (step P24, process flow F4). In some embodiments, by using the cell monitoring apparatus S3, it may be possible to monitor the three-dimensional aggregates 920 without harvesting the three-dimensional aggregates 920 from the culturing environment (e.g., the micro-wells 1216A-1216C).

In some alternative embodiments, the experiment may continue after the first data point is acquired. In some embodiments, the distances D1 and D2 between the bottom surface 1200b of the channel module 1200 and the top surface 1100t of the sensing chip 1100 in correspondence of the microchannels 1213, 1214 and the culture chamber 1215 may be such that the three-dimensional aggregates 920 are trapped within the areas of the corresponding micro-wells 1216A-1216C. That is, the three-dimensional aggregates 920 may be prevented from migrating between adjacent micro-wells 1216A-1216C as well as entering the microchannels 1213 or 1214. In this way, it may be possible to follow-up for extended times the micro-physiological state of the three-dimensional aggregates 920 without need to harvest them. In some embodiments, if the data points are acquired with the cell monitoring apparatus S3 oriented as illustrated in FIG. 15C, the three-dimensional aggregates 920 may be cultivated for additional times (step P22, process flow F5), and the measuring step P18 may be repeated as many time as necessary (process flow F6).

As discussed above, in some embodiments the cell monitoring apparatus S3 may be flipped upside down during the measuring phases (steps P16, P18, process flow F2, F3), so that the three-dimensional aggregates 920 move closer to the corresponding sensing areas 1112A-1112C. After the data are acquired, the cell monitoring apparatus S3 may be re-positioned as illustrated in FIG. 15C (step P20, process flow F7), so that the three-dimensional aggregates 1112A-1112C may proceed towards the bottom of the corresponding micro-wells 1216A-1216C, where they may be cultured (step P22, process flow F8) until it is time for the next measurement (step P16 according to process flow F9, or step P18, according to process flow F6). Because the three-dimensional aggregates 920 are not harvested from the cell monitoring system S3 to perform measurements, data acquisition (step P18) and further culture (step P22) may continue for as long as desired before the experiment is terminated (step P24).

As a way of example, the cell monitoring apparatus S3 may be used to monitor the activity of an embryoid body formed by mouse embryonic stem cells (mESCs). For example, a suspension of mESCs may be introduced in the cell monitoring apparatus S3 after the mESCs have been separated from the mouse embryonic fibroblasts (MEF) of the feeder layer (step P12). The separation may be achieved, for example, via one or more incubation (e.g., 1-40 min, 37° C., 5% $CO_2$) and centrifugation steps (e.g., at about 250×g for about 5 minutes). After separation of the mESCs from the feeder layer, the cell concentration of the suspension may be adjusted to the desired value (e.g., $1 \times 10^5$ cells/mL). An aliquot of the mESCs suspension (e.g., 0.5 mL) may be introduced in the cell monitoring apparatus S3 (as described above, e.g., with respect to FIG. 15B). The mESCs may then be cultured in the cell monitoring apparatus S3 for the desired time (step P14). For example, the mESCs may be cultured for about two weeks in an incubator at 37° C., in an atmosphere including about 5% of $CO_2$, until mouse embryoid bodies (EBs) are formed in the micro-wells 1216 (as described above, e.g., with respect to FIG. 15C). The embryoid bodies may then be cultured in the micro-wells 1216 for the desired period of time. For example, the embryoid bodies may be cultured in the micro-wells 1216 for about two weeks, until a "beating" appears. The beating of the embryoid bodies may then be monitored by the sensing chip 1100 (as illustrated, e.g., in FIG. 15D, step P18). For example, the sensing chip 1100 may detect the release of calcium ions from the embryoid bodies. What is more, after the first measurement it may be possible to keep culturing the embryoid bodies in the micro-wells 1216 of the cell monitoring apparatus S3 for extended period of times (step P22), and repeat the measurements (process flows F6 or F9) to acquire more time points during the extended culturing time. That is, the steps P18 and P22 may be alternately repeated for the desired duration of the experiment. While culturing, the spent medium may be replaced as required, for example, every other day.

Based on the above, with the cell monitoring apparatus according to the embodiments of the present disclosure, it is possible to culture and monitor in real time the micro-physiological responses from three-dimensional cellular aggregates, without need of harvesting the aggregates. Therefore, the cell monitoring apparatus disclosed here allows long-term monitoring of the physiological states and responses of three-dimensional cellular aggregates in physiologically relevant conditions. According to some embodiments, the cell monitoring apparatus may provide a low-cost, accurate, and reliable solution for long-term testing of drugs effects or stress response.

According to some embodiments, a cell monitoring apparatus includes a sensing chip and a channel module. The sensing chip includes a channel region, a pair of source and drain regions, and a sensing film. The channel region includes a first semiconductor material. The pair of source and drain regions is disposed at opposite sides of the channel region, and includes a second semiconductor material. The sensing film is disposed on the channel region at a sensing surface of the sensing chip. The channel module is disposed on the sensing surface of the sensing chip. A micro fluidic channel is formed between the sensing surface of the sensing chip and a surface of the channel module proximal to the sensing chip. The microfluidic channel includes a culture chamber and a micro-well. The culture chamber is concave into the proximal surface of the channel module, at a region of the proximal surface of the channel module overlying the channel region. The micro-well is concave into a side of the culture chamber, and directly faces the sensing film.

According to some embodiments, a cell monitoring apparatus includes a sensing chip and a channel module. The sensing chip includes a substrate and a sensing region formed in the substrate at a sensing surface of the sensing chip. The channel module is disposed on the sensing chip, with a proximal surface directly opposite the sensing surface of the sensing chip. The channel module has a first microchannel, a second microchannel, a first microtrench, a second microtrench, and a first recess. The first microchannel extends along a first direction from the proximal surface of the channel module to a surface of the channel module distal to the sensing chip. The distal surface and the proximal surface of the channel module are opposite to each other. The second microchannel extends from the distal surface of the channel module to the proximal surface of the channel module along the first direction. The first microtrench is located at the proximal surface of the channel module, at one end of the first microchannel. The first microtrench extends from the first microchannel towards the second microchannel along a second direction different from the first direction. The second microtrench is located at the proximal surface of the channel module at one end of the second microchannel. The second microtrench extends from the second microchannel towards the first microchannel along a third direction different from the first direction. The first recess is located between the first microtrench and the second microtrench. The first recess directly faces the sensing region of the sensing chip. The first microchannel, the first microtrench, the first recess, the second microtrench, and the second microchannel are connected to each other, in this order.

According to some embodiments, a cell monitoring method employs a cell monitoring apparatus. The cell monitoring apparatus includes a sensing chip and a channel module. The sensing chip includes a substrate. A sensing region is located in the substrate at a sensing surface of the sensing chip. The channel module is disposed on the sensing surface of the sensing chip with a proximal surface facing the sensing chip. A micro-well concave in the proximal surface is opposite to the sensing region. The cell monitoring method includes the following steps. A culture medium is introduced in the cell monitoring apparatus. The culture medium includes cells. The cells are cultivated in the micro-well for a first period of time. The cells form a three-dimensional aggregate in the micro-well during the first period of time. The presence of a target analyte produced by the three-dimensional aggregate is detected through a signal generated in the sensing region of the sensing chip.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure.

What is claimed is:

1. A cell monitoring apparatus, comprising:
    a sensing chip, comprising:
        a channel region comprising a first semiconductor material;
        a pair of source and drain regions disposed at opposite sides of the channel region and comprising a second semiconductor material; and
        a sensing film disposed on the channel region at a sensing surface of the sensing chip; and
    a channel module, disposed on the sensing surface of the sensing chip, and has a proximal surface facing the sensing surface of the sensing chip and a distal surface opposite to the proximal surface,
    wherein a microfluidic channel is disposed between the sensing surface of the sensing chip and the proximal surface of the channel module, the microfluidic channel comprising:
        a culture chamber, concave into the proximal surface of the channel module, wherein the culture chamber comprises a bottom surface, a first level height of the bottom surface is between a second level height of the proximal surface and a third level height of the distal surface; and
        a micro-well, concave into the bottom surface of the culture chamber, wherein the micro-well is located at a level height between the first level height and the third level height.

2. The cell monitoring apparatus of claim 1, wherein the channel module comprises:
    a first region of a polymeric material having a first thickness, wherein the first region extends from the proximal surface of the channel module to the distal surface of the channel module;
    a second region of the polymeric material having a second thickness, wherein the second thickness is smaller than the first thickness, and the second region extends from the bottom surface of the culture chamber to the distal surface of the channel module; and
    a third region of the polymeric material having a reducing thickness,
    wherein the second region of the polymeric material surrounds the third region of the polymeric material, and a maximum thickness of the third region is equal to the second thickness.

3. The cell monitoring apparatus of claim 1, wherein the microfluidic channel further comprises microchannels extending from different sides of the culture chamber to the distal surface of the channel module.

4. The cell monitoring apparatus of claim 3, further comprising a cover module disposed on the channel module, wherein the cover module includes a region having a pair of through holes extending through the cover module, a first microchannel of the microchannels is directly connected to one through hole of the pair, and a second microchannel of the microchannels is directly connected to the other through hole of the pair.

5. The cell monitoring apparatus of claim 4, further comprising a carrier substrate, wherein the sensing chip and the cover module are disposed on the carrier substrate, the sensing chip is disposed between the channel module and the carrier substrate, and the sensing chip is electrically connected to the carrier substrate.

6. The cell monitoring apparatus of claim 4, further comprising a base module, wherein the channel module and the sensing chip are disposed between the base module and the cover module, and the cover module is fastened to the base module.

7. A cell monitoring apparatus, comprising:
    a sensing chip, comprising:
        a channel region comprising a semiconductor material; and
        a sensing film disposed on the channel region at a sensing surface of the sensing chip; and
    a channel module, disposed on the sensing surface of the sensing chip and has a proximal surface facing the sensing surface of the sensing chip and a distal surface opposite to the proximal surface,
    wherein a microfluidic channel is disposed between the sensing surface of the sensing chip and the proximal surface of the channel module, the microfluidic channel comprising:
        a first microchannel, extending along a first direction from the proximal surface of the channel module to the distal surface of the channel module;
        a second microchannel, extending from the distal surface of the channel module to the proximal surface of the channel module along the first direction;
        a third microchannel, located at the proximal surface of the channel module at one end of the first microchannel, and extending from the first microchannel towards the second microchannel along a second direction different from the first direction;
        a fourth microchannel, located at the proximal surface of the channel module at one end of the second microchannel, and extending from the second microchannel towards the first microchannel along a third direction different from the first direction;
        a culture chamber, located between the third microchannel and the fourth microchannel, and concave into the proximal surface of the channel module, wherein the culture chamber extends from the proximal surface of the channel module toward the distal surface of the channel module, and forms a first surface at a first level; and
        a micro-well, concave into a side of the first surface of the culture chamber, wherein the micro-well directly faces the sensing film, extends from the first surface of the culture chamber toward the distal surface of the channel module, and form a second surface having a topmost at a second level facing away from the sensing surface of the sensing chip, wherein the first microchannel, the third microchannel, the culture chamber, the fourth microchannel, and the second microchannel are connected to each other in order, the proximal surface of the channel module is separated from the sensing surface of the sensing chip with a first distance, a distance between the first level of the first surface of the culture chamber and the sensing surface of the sensing chip is a second distance, a distance between the second level of the second surface of the micro-well and the sensing surface of the sensing chip is a third distance, and the third distance is greater than the second distance, and the second distance is greater than the first distance.

8. The cell monitoring apparatus of claim 7, wherein the third microchannel extends from the first microchannel to a first side of the culture chamber, the fourth microchannel extends from the second microchannel to a second side of the culture chamber, and the micro-well opens on a third side of the culture chamber, wherein the first side, the second side, and the third side are different sides of the culture chamber.

9. The cell monitoring apparatus of claim 8, wherein multiple micro-wells open on the third side of the culture chamber.

10. The cell monitoring apparatus of claim 7, wherein the second direction and the third direction are the same.

11. The cell monitoring apparatus of claim 7, further comprising:

an anti-adhesion layer, disposed on the proximal surface of the channel module within the microfluidic channel.

12. The cell monitoring apparatus of claim 11, wherein the anti-adhesion layer comprises albumin, polyhydroxyethyl methacrylate, polyethylene glycol, or 2-methacryloyloxy-ethylphosphorylcholine.

13. A cell monitoring apparatus, comprising:

a sensing chip comprising a transistor having a channel region;

a sensing film covering the channel region;

a channel module disposed over the sensing chip, the channel module comprising a first surface facing the sensing chip and a second surface opposite to the first surface, wherein a microfluidic channel is between the sensing chip and the first surface of the channel module, and the microfluidic channel comprises:

a culture chamber, concave into the first surface of the channel module wherein the culture chamber comprises a bottom surface; and a micro-well, concave into the bottom surface of the culture chamber.

14. The cell monitoring apparatus of claim 13, wherein the channel module comprises:

a first region of a polymeric material having a first thickness, wherein the first region extends from the first surface of the channel module to the second surface of the channel module; and a second region of the polymeric material having a second thickness, wherein the second thickness is smaller than the first thickness, and the second region extends from the bottom surface of the culture chamber to the second surface of the channel module.

15. The cell monitoring apparatus of claim 14, wherein the channel module further comprises a third region of the polymeric material having a reducing thickness, wherein the second region of the polymeric material surrounds the third region of the polymeric material, and a maximum thickness of the third region is substantially equal to the second thickness.

16. The cell monitoring apparatus of claim 13, wherein the microfluidic channel further comprises microchannels extending from different sides of the culture chamber to the second surface of the channel module.

17. The cell monitoring apparatus of claim 16, further comprising a cover module disposed on the channel module, wherein the cover module includes a region having a pair of through holes, a first microchannel among the microchannels is connected to a first through hole among the pair of through holes, and a second microchannel of the microchannels is connected to a second through hole among the pair of through holes.

18. The cell monitoring apparatus of claim 17, further comprising a carrier substrate, wherein the sensing chip and the cover module are disposed on the carrier substrate, the sensing chip is disposed between the channel module and the carrier substrate, and the sensing chip is electrically connected to the carrier substrate.

19. The cell monitoring apparatus of claim 17, further comprising a base module, wherein the channel module and the sensing chip are disposed between the base module and the cover module, and the cover module is fastened to the base module.

20. The cell monitoring apparatus of claim 13, wherein a first level height of the bottom surface is between a second level height of the first surface and a third level height of the second surface, and wherein the micro-well is located at a level height between the first level height and the third level height.

* * * * *